United States Patent
Yuyama et al.

(10) Patent No.: US 9,790,017 B2
(45) Date of Patent: Oct. 17, 2017

(54) TABLET FEEDER AND PHARMACY SYSTEM

(71) Applicant: YUYAMA MFG. CO., LTD., Toyonaka-shi, Osaka (JP)

(72) Inventors: Shoji Yuyama, Toyonaka (JP); Naoki Koike, Toyonaka (JP); Takafumi Imai, Toyonaka (JP); Yoshinori Kumano, Toyonaka (JP); Akira Maeda, Toyonaka (JP); Mitsuhiro Mitani, Toyonaka (JP)

(73) Assignee: YUYAMA MFG. CO., LTD., Osaka (JP)

( * ) Notice: Subject to any disclaimer, the term of this patent is extended or adjusted under 35 U.S.C. 154(b) by 35 days.

(21) Appl. No.: 14/601,910

(22) Filed: Jan. 21, 2015

(65) Prior Publication Data
US 2015/0197391 A1 Jul. 16, 2015

Related U.S. Application Data

(63) Continuation-in-part of application No. 13/715,525, filed on Dec. 14, 2012, now Pat. No. 8,944,280.
(Continued)

(30) Foreign Application Priority Data

Nov. 21, 2008 (JP) .................................. 2008-298122
Mar. 2, 2009 (JP) .................................. 2009-048442
Aug. 24, 2009 (JP) .................................. 2009-193142

(51) Int. Cl.
*G07F 11/00* (2006.01)
*B65H 3/44* (2006.01)
(Continued)

(52) U.S. Cl.
CPC .............. *B65D 83/04* (2013.01); *B65B 5/103* (2013.01); *G07F 11/18* (2013.01); *G07F 11/62* (2013.01);
(Continued)

(58) Field of Classification Search
CPC ......... B65D 83/04; B65D 5/103; G07F 11/18; G07F 11/62; G07F 17/0092; G06F 19/3462
(Continued)

(56) References Cited

U.S. PATENT DOCUMENTS 4,551,024 A * 11/1985 Clapp ................... B28C 9/0463
366/347
4,664,289 A 5/1987 Shimizu et al.
(Continued)

FOREIGN PATENT DOCUMENTS

EP 1 477 403 A1 11/2004
JP 4-049044 Y2 2/1992
(Continued)

OTHER PUBLICATIONS

English translation and the PCT International Search Report in Japanese language dated Dec. 15, 2009 which is issued in a related PCT International Application No. PCT/JP2009/006195 (4 pages).
(Continued)

*Primary Examiner* — Rakesh Kumar
(74) *Attorney, Agent, or Firm* — Robert P. Michal, Esq.; Carter, DeLuca, Farrell & Schmidt, LLP

(57) ABSTRACT

A tablet feeder comprises a device body, a plurality of tablet cassettes disposed on one face of the device body 1 in a vertical direction, each tablet cassette accommodating a plurality of tablets by kind, and a plurality of chutes disposed on one face of the device body 1 in a vertical direction and shifted in a horizontal direction, the chutes temporarily
(Continued)

storing the tablets dispensed from the tablet cassette and having the dispensing portion at the downward portion thereof, the dispensing portion being capable of dispensing the tablets to a bottomed cylindrical tablet container.

6 Claims, 33 Drawing Sheets

Related U.S. Application Data which is a continuation of application No. 13/018,564, filed on Feb. 1, 2011, now Pat. No. 8,579,153, which is a continuation-in-part of application No. PCT/JP2009/006195, filed on Nov. 18, 2009.

(51) Int. Cl.
| | | |
|---|---|---|
| B65D 83/04 | (2006.01) | |
| B65B 5/10 | (2006.01) | |
| G07F 11/18 | (2006.01) | |
| G07F 11/62 | (2006.01) | |
| G07F 17/00 | (2006.01) | |
| G06F 19/00 | (2011.01) | |

(52) U.S. Cl.
CPC ...... *G07F 17/0092* (2013.01); *G06F 19/3462* (2013.01)

(58) Field of Classification Search
USPC .......... 700/231, 244, 236, 242; 53/493, 508; 364/479.01; 221/122, 130
See application file for complete search history.

(56) References Cited

U.S. PATENT DOCUMENTS

| | | | |
|---|---|---|---|
| 5,354,127 A * | 10/1994 | Del Zotto | B01F 7/087 366/186 |
| 5,678,393 A | 10/1997 | Yuyama et al. | |
| 5,709,063 A * | 1/1998 | Yuyama | B65B 1/06 53/154 |
| 5,787,678 A * | 8/1998 | Koike | B65B 39/002 221/124 |
| 5,860,563 A | 1/1999 | Guerra et al. | |
| 5,927,546 A | 7/1999 | Yuyama et al. | |
| 6,170,229 B1 | 1/2001 | Kim | |
| 6,349,848 B1 | 2/2002 | Uema et al. | |
| 6,405,893 B1 | 6/2002 | Tobe et al. | |
| 6,471,088 B1 * | 10/2002 | Uema | G07F 9/02 221/13 |
| 6,471,090 B1 * | 10/2002 | Inamura | G07F 11/44 221/124 |
| 6,497,339 B1 * | 12/2002 | Geltser | A61J 7/02 198/766 |
| 6,554,157 B2 * | 4/2003 | Geltser | A61J 7/02 221/200 |
| 6,595,384 B2 | 7/2003 | Takahashi | |
| 6,644,504 B2 | 11/2003 | Yuyama et al. | |
| 6,928,790 B2 * | 8/2005 | Takahashi | B65B 5/103 221/251 |
| 6,988,464 B1 | 1/2006 | Rutledge | |
| 7,014,063 B2 | 3/2006 | Shows et al. | |
| 7,016,766 B2 | 3/2006 | William et al. | |
| 7,040,070 B2 | 5/2006 | Yuyama et al. | |
| RE40,453 E * | 8/2008 | Lasher | G07F 5/18 221/174 |
| 7,412,302 B2 * | 8/2008 | Cobb | G07F 17/0092 700/231 |
| 7,419,042 B2 | 9/2008 | Enomoto et al. | |
| 7,455,163 B2 * | 11/2008 | Yuyama | B65B 35/04 193/2 R |
| 7,747,345 B2 * | 6/2010 | Ohmura | G06F 19/3462 700/231 |
| 7,861,492 B2 * | 1/2011 | Yuyama | B65B 5/103 221/2 |
| 8,061,560 B2 * | 11/2011 | Farnsworth | B65B 39/001 221/234 |
| 8,090,471 B2 * | 1/2012 | Shows | G06F 19/3462 221/2 |
| 8,141,330 B2 * | 3/2012 | Henkel | B65B 5/103 53/237 |
| 8,261,936 B2 * | 9/2012 | Dumond | G07F 11/44 198/399 |
| 8,281,955 B2 * | 10/2012 | Farnsworth | B65B 39/001 221/234 |
| 9,299,210 B2 * | 3/2016 | Parrish | G07F 9/026 |
| 2002/0007868 A1 | 1/2002 | Kodama et al. | |
| 2003/0074868 A1 * | 4/2003 | Yasuoka | B65B 5/103 53/493 |
| 2004/0176873 A1 * | 9/2004 | Kim | G07F 11/44 700/231 |
| 2005/0189365 A1 * | 9/2005 | Geltser | A61J 7/02 221/7 |
| 2005/0234591 A1 | 10/2005 | Kim | |
| 2005/0263051 A1 * | 12/2005 | Harnetiaux | A01C 7/081 111/174 |
| 2006/0060596 A1 * | 3/2006 | Shigeyama | B65B 5/08 221/11 |
| 2006/0076358 A1 * | 4/2006 | Shigeyama | B65G 59/067 221/104 |
| 2006/0230710 A1 | 10/2006 | Ishiwatari et al. | |
| 2007/0095262 A1 * | 5/2007 | Harnetiaux | A01C 7/081 111/170 |
| 2007/0136376 A1 * | 6/2007 | Kusakabe | G06F 19/3456 |
| 2007/0150092 A1 * | 6/2007 | Ohmura | G06F 19/3462 700/231 |
| 2008/0255700 A1 * | 10/2008 | Mitchell | A61J 7/02 700/240 |
| 2009/0039097 A1 * | 2/2009 | Farnsworth | G07F 11/44 221/1 |
| 2009/0043421 A1 * | 2/2009 | Parrish | G07F 9/026 700/241 |
| 2009/0140002 A1 * | 6/2009 | Farnsworth | B65B 39/001 221/178 |
| 2010/0229506 A1 * | 9/2010 | Kumano | G07F 17/0092 53/493 |
| 2011/0160901 A1 | 6/2011 | Abrams, Jr. et al. | |
| 2011/0178634 A1 | 7/2011 | Yuyama et al. | |
| 2012/0061417 A1 * | 3/2012 | Farnsworth | B65B 39/001 221/124 |
| 2012/0116579 A1 | 5/2012 | Shows et al. | |
| 2012/0253839 A1 | 10/2012 | Berzansky et al. | |
| 2015/0197391 A1 * | 7/2015 | Yuyama | B65D 83/04 221/2 |

FOREIGN PATENT DOCUMENTS

| | | |
|---|---|---|
| JP | 5-032408 Y2 | 8/1993 |
| JP | 9-253169 A | 9/1997 |
| JP | 2000-103404 A | 4/2000 |
| JP | 2001-233306 A | 8/2001 |
| JP | 2002-029511 A | 1/2002 |
| JP | 3373505 B2 | 2/2003 |
| JP | 2003-237712 A | 8/2003 |
| JP | 2003-291901 A | 10/2003 |
| WO | WO 0018646 A1 | 4/2000 |
| WO | WO 03/070575 A1 | 8/2003 |

OTHER PUBLICATIONS

English translation of PCT International Preliminary Report on Patentability and Written Opinion mailed Jun. 30, 2011 which is issued in a related PCT International Application No. PCT/JP2009/006195 (6 pages).

(56) References Cited

OTHER PUBLICATIONS

Notice of Allowance and Notice of Allowability mailed Sep. 5, 2013, which was issued in a related U.S. Appl. No. 13/018,564 (14 pages).

* cited by examiner

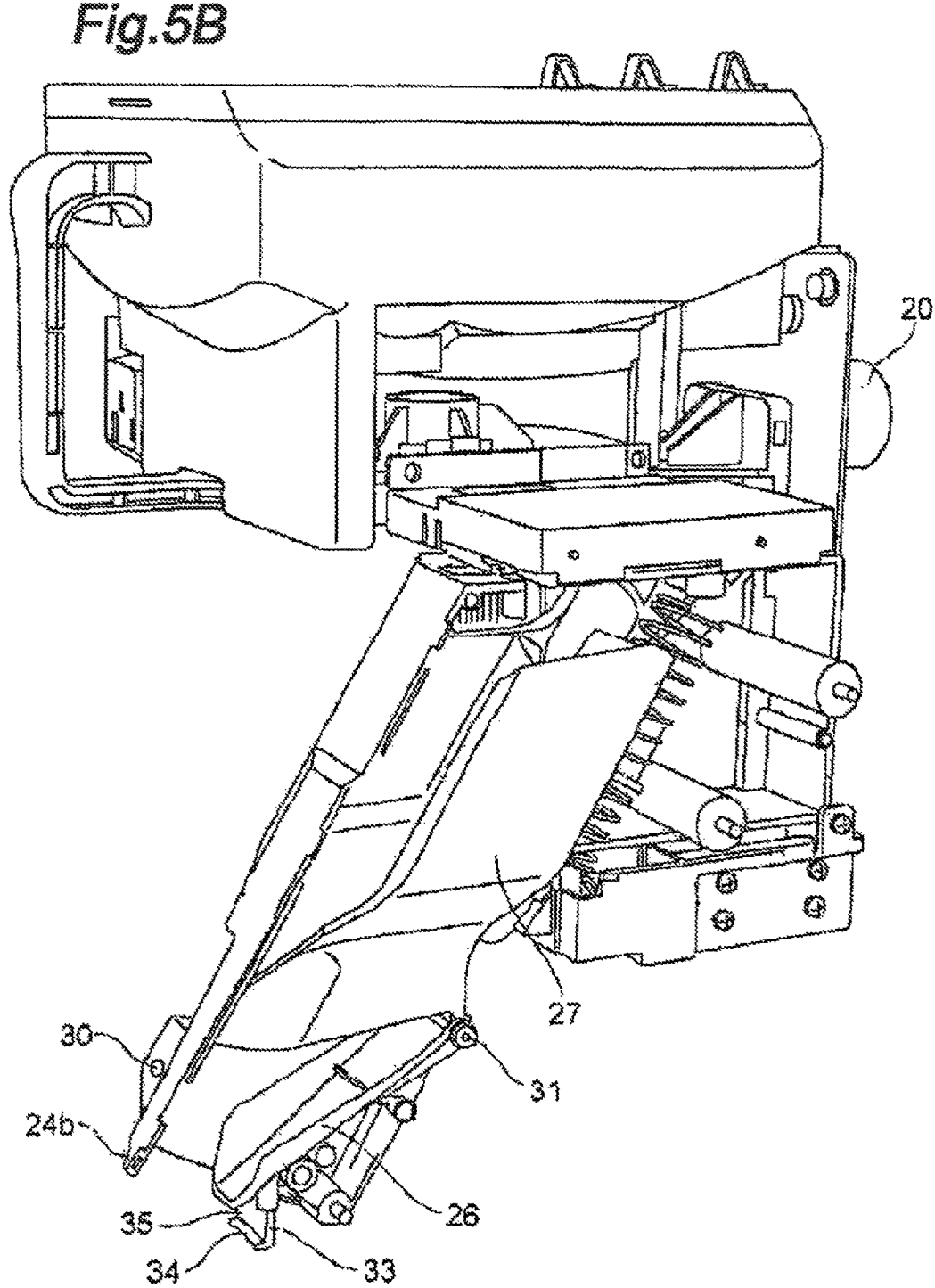

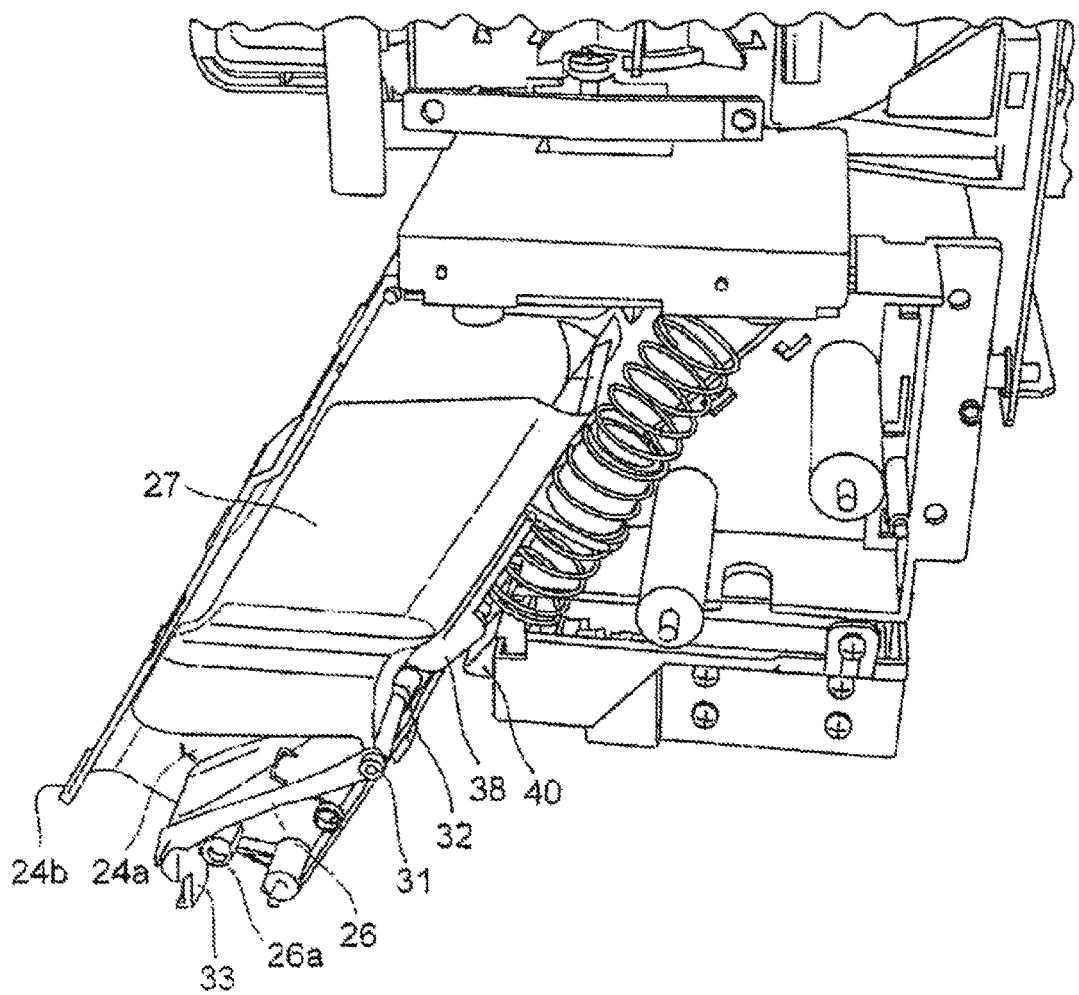

Fig. 8

CASSETTE INFORMATION

| 001 xxxxxxx | 010 xxxxxxx | 019 xxxxxxx | 028 xxxxxxx | 037 xxxxxxx | 046 xxxxxxx |
|---|---|---|---|---|---|
| 002 xxxxxxx | 011 xxxxxxx | 020 xxxxxxx | 029 xxxxxxx | 038 xxxxxxx | 047 xxxxxxx |
| 003 xxxxxxx | 012 xxxxxxx | 021 xxxxxxx | 030 xxxxxxx | 039 xxxxxxx | 048 xxxxxxx |
| 004 xxxxxxx | 013 xxxxxxx | 022 xxxxxxx | 031 xxxxxxx | 040 xxxxxxx | 049 xxxxxxx |
| 005 xxxxxxx | 014 xxxxxxx | 023 xxxxxxx | 032 xxxxxxx | 041 xxxxxxx | 050 xxxxxxx |
| 006 xxxxxxx | 015 xxxxxxx | 024 xxxxxxx | 033 xxxxxxx | 042 xxxxxxx | 051 xxxxxxx |
| 007 xxxxxxx | 016 xxxxxxx | 025 xxxxxxx | 034 xxxxxxx | 043 xxxxxxx | 052 xxxxxxx |
| 008 xxxxxxx | 017 xxxxxxx | 026 xxxxxxx | 035 xxxxxxx | 044 xxxxxxx | 053 xxxxxxx |
| 009 xxxxxxx | 018 xxxxxxx | 027 xxxxxxx | 036 xxxxxxx | 045 xxxxxxx | 054 xxxxxxx |

<< Unit 1 1-64 >>

MENU | Prescription List | Exception List | Drug List | Information | Manual

41

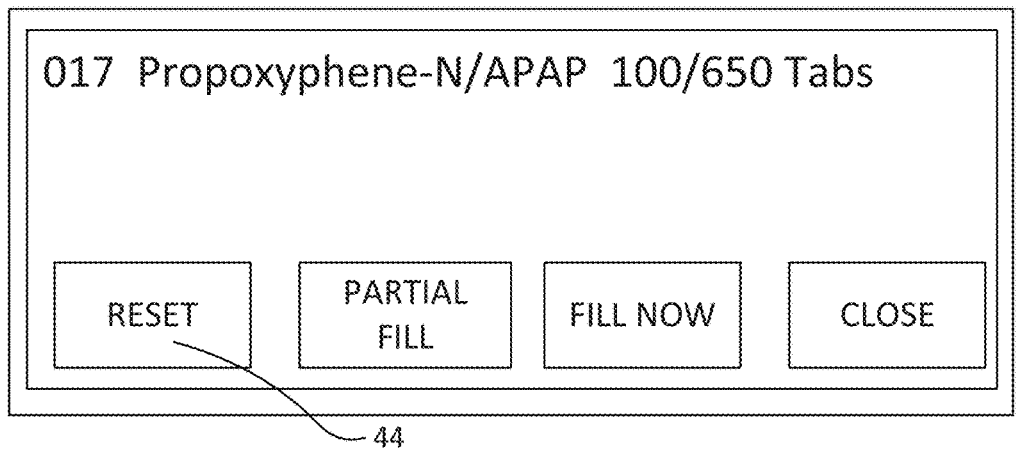

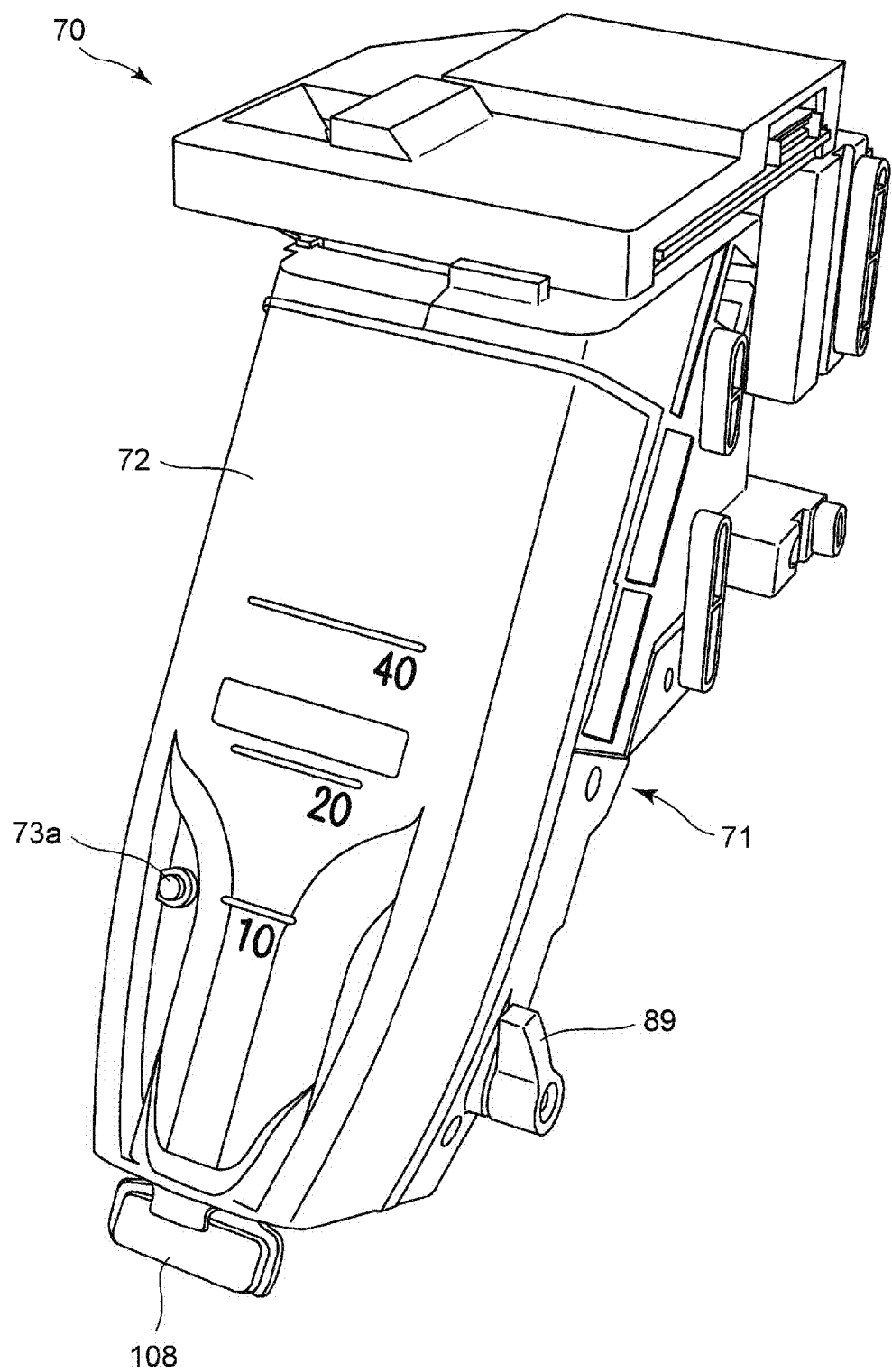

TABLET FEEDER AND PHARMACY SYSTEM

CROSS-REFERENCE TO RELATED APPLICATIONS

This is a Continuation-In-Part Application of U.S. patent application Ser. No. 13/715,525 filed on Dec. 14, 2012, now U.S. Pat. No. 8,944,280, which is a Continuation of U.S. patent application Ser. No. 13/018,564 filed on Feb. 1, 2011, now U.S. Pat. No. 8,579,153, which is a Continuation-In-Part of PCT International Application No. PCT/JP2009/006195 filed on Nov. 18, 2009, which in turn claims the benefit of foreign priority under 35 U.S.C. §119 to Japanese Patent Application Nos. JP2009-193142 filed on Aug. 24, 2009, JP2009-048442 filed on Mar. 2, 2009, and JP2008-298122 filed on Nov. 21, 2008, the entire disclosure of each of which is incorporated herein by reference.

BACKGROUND

1. Technical Field

The present invention relates to a tablet feeder and pharmacy system.

2. Description of the Related Art

Conventionally, it is well-known as a tablet feeder that a plural of bins in which tablets are accommodated are disposed on one side face of a frame, while chutes which respectively guide the tablets dispensed from the each bin are disposed on the opposed face thereof. (See US 2011/0160901)

However, the tablet feeder is only configured so that the chute is provided on the back side thereof with respect to the bin. Such a configuration is not available in the case of providing the both of the bin and chute with the front side of the apparatus or providing them with the front and back side thereof respectively.

SUMMARY

Thus, it is an object of the present invention to provide the tablet feeder on which can arrange the tablet cassettes and chutes in several manners and in a high density, and pharmacy system on which the tablet feeder is located.

In order to resolve the aforementioned problems, the present invention provides a tablet feeder characterized in comprising:
  a device body;
  a plurality of tablet cassettes disposed on one face of the device body in a vertical direction, each tablet cassette accommodating a plurality of tablets by kind;
  a plurality of chutes disposed on one face of the device body in a vertical direction and shifted in a horizontal direction, the chutes temporarily storing the tablets dispensed from the tablet cassette and having the dispensing portion at the downward portion thereof, the dispensing portion being capable of dispensing the tablets to a bottomed cylindrical tablet container.

With this configuration, the line of the tablet cassettes and chutes can be shifted in a horizontal direction. This allows the tablet cassettes and chutes to layout in various aspects. The whole of the configuration can be formed as a slim form in a front-back direction.

Preferably, the tablet feeder further includes a passage member for guiding the tablets dispensed from the tablet cassette to the other face side positioned at the opposite side to the one face, wherein the chutes are arranged at the other face of the device body in a vertical direction and capable of storing the tablets dispensed from the tablet cassette through the passage member.

With this configuration, it is possible to fill up tablets in the tablet cassette at one face side of the device body and to dispense tablets from the chute at the other face side opposed to the device body. This allows a number of operators to perform the each works simultaneously and to increase efficiency of the each works.

Preferably, the tablet cassettes are further disposed on the opposite side to the one face of the device body in a vertical direction; the chutes are disposed adjacent to the tablet cassettes arranged at the same face of the device body in a vertical direction.

With this configuration, it is possible to dispose the tablet cassettes and chutes in the high density by effectively utilizing the limited space of the device body.

Preferably, the tablet cassettes and chutes are respectively disposed on one and the other area separated in a horizontal direction of one and the other face of the device body.

With this configuration, it is possible to prevent the area on which the cassettes are provided and the area on which the chutes are provided from being mixed and to perform the work of filling up and dispensing tablets effectively.

Preferably, the passage member is formed so that the passage section in which the tablets move makes its cross-sectional area wider from the tablet cassettes toward the chutes, With this configuration, it is possible to prevent tablets from clogging in the passage member when tablets move therethrough, Preferably, the passage member has a detection sensor for detecting the clog of tablets in the passage member.

With this configuration, it is possible to immediately detect the clog of tablets by the detection sensor for detecting the clog of tablets even if the tablets are clogged in the passage member.

Preferably, the each cassette is detachably attached to the device body independently from the attachment of the each corresponding chute to the device body, the corresponding chute keeps the condition of the attachment to the device body, the chute has an inlet and an outlet, the inlet is adjacent to the tablet cassette, the outlet extends from the one face of the device body.

With this configuration, it is possible to attach or detach the tablet cassettes and chutes to or from the device body individually.

Preferably, the chute extends in a downward direction away from the one face of the device body, the lower portion of the chute is provided so as to overlap the upper portion of the second chute provided at the lower side of the first chute, the second chute acts so as to guide a tablet container in which tables are dispensed from the first chute.

With this configuration, it is possible to perform the work of dispensing tablets to the tablet container by hand work easily and certainly.

Preferably, the chute has an opening for dispensing tablets, each opening degree is adjustable depending on the size of the opening end of the tablet container where tablets are dispensed.

With this configuration, it is possible to prevent the tablets from falling down around the chute to dispense them into the tablet cassette certainly by decreasing the size of the opening area of the dispensing portion if the size of the opening portion of the tablet cassette is small, while by increasing it if it is large.

Preferably, the chute has a gate member which can open and close the opening, the tablets are dispensed through the opening of the chute when the opening is opened.

Preferably, the chute has a chute body and a cover which is detachable to the chute body.

Preferably, the chute has a lock mechanism to lock the cover in the condition that the cover is attached to the chute body.

Preferably, the tablet feeder further comprises a first control member to control a plurality of chutes so as to dispense tablets by driving one of the cassettes in which an appropriate number of tablets are accommodated, when the tablet which should be dispensed to the chute is included in the next prescription data, the first control member temporarily stops to dispense tablets from the tablet cassette until tablets are dispensed from the chute.

Preferably, the tablet feeder further comprises a display member displaying a standby prescription number.

Preferably, the display member is provided on the face except the one face, the other face or the bottom face of the device body so as to be able to change the direction of the display face.

In order to resolve the aforementioned problems, the present invention provides a tablet feeder characterized in comprising:

a tablet feeder including a device body, a plurality of tablet cassettes provided on the one face of the device body in a vertical direction, and a plurality of chutes disposed on one face of the device body in a vertical direction and shifted in a horizontal direction, the chutes temporarily storing the tablets dispensed from the tablet cassette and having the dispensing portion at the downward portion thereof, the dispensing portion being capable of dispensing the tablets to a bottomed cylindrical tablet container;

a tablet delivery area extending from one end side to one direction of the other end side, wherein the tablet feeder is disposed so that one face or the other face thereof is positioned at the straight line extending from the other direction crossing the one direction with respect to the tablet delivery area, With this configuration, it is possible to perform the work of filling up tablets into the tablet cassette and In order to resolve the aforementioned problems, the present invention provides a pharmacy system characterized in comprising:

a tablet feeder including a device body, a plurality of tablet cassettes provided on the one face of the device body in a vertical direction, and a plurality of chutes disposed on one face of the device body in a vertical direction and shifted in a horizontal direction, the chutes temporarily storing the tablets dispensed from the tablet cassette and having the dispensing portion at the downward portion thereof, the dispensing portion being capable of dispensing the tablets to a bottomed cylindrical tablet container;

a tablet delivery area extending from one end side to one direction of the other end side, wherein the tablet feeder is disposed so that one face or the other face thereof is positioned at the straight line extending from the other direction crossing the one direction with respect to the tablet delivery area.

With this configuration, the tablet cassettes and chutes can be arranged on the tablet feeder in high density.

Preferably, the chutes are arranged on the tablet delivery area side.

With this configuration, it is possible to reduce the distance when delivering tablets to a patient and to perform the work efficiency.

In order to resolve the aforementioned problems, the present invention provides a tablet feeder characterized in comprising:

a tablet feeder including a device body, a plurality of tablet cassettes provided on the one face of the device body in a vertical direction, and a plurality of chutes disposed on one face of the device body in a vertical direction and shifted in a horizontal direction, the chutes temporarily storing the tablets dispensed from the tablet cassette and having the dispensing portion at the downward portion thereof, the dispensing portion being capable of dispensing the tablets to a bottomed cylindrical tablet container;

a tablet delivery area extending from one end side to one direction of the other end side, wherein the two tablet feeders are provided so that one face of one of them and the other opposite face of the other of them are back to back, the one face or the other opposite face are positioned on the straight line extending to the other direction crossing the one direction.

According to the present invention, it is possible to effectively perform the mounting work to the device body since the tablet cassettes and chutes are arranged in different vertical rows.

BRIEF DESCRIPTION OF THE DRAWINGS

FIG. 5B is a perspective view showing the chute shown of FIG. 1 with the second cassette removed.

FIG. 5C is a perspective view showing the chute of FIG. 5B seen from a different angle.

FIG. 8 shows the main screen displayed in the liquid crystal monitor of FIG. 1.

FIG. 10 shows the dispensing information screen displayed in response to touch operations of the tablet cassette area on the main screen of FIG. 8.

FIG. 11 shows the manual input screen displayed on the liquid crystal monitor of FIG. 1.

FIG. 12 is a perspective view of the chute according to another embodiment.

PREFERRED EMBODIMENT

Figure 1:
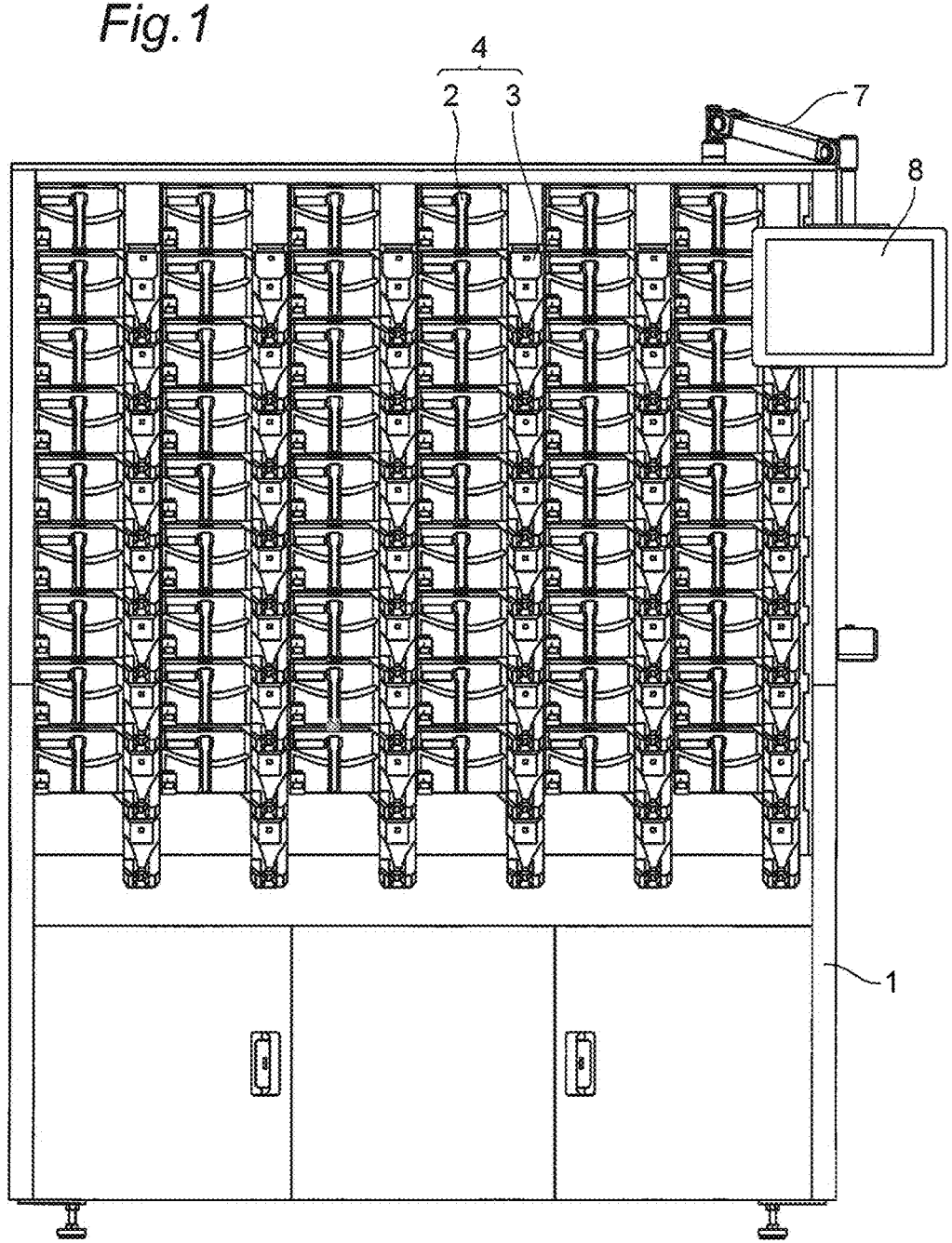
FIG. 1 is a front view of the tablet feeder according to the present embodiment.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the mechanism and designated parts thereof. Unless specifically set forth herein, the terms "a", "an" and "the" are not limited to one element but instead should be read as meaning "at least one". Terms, such as "above," "below," "side," and "end," will be used as necessary and are being used to facilitate understanding of the invention in reference to the drawings and the meanings of such terms do not place limitations on the technical scope of the present invention. The terminology includes the words noted above, derivatives thereof and words of similar import.

Figure 2:
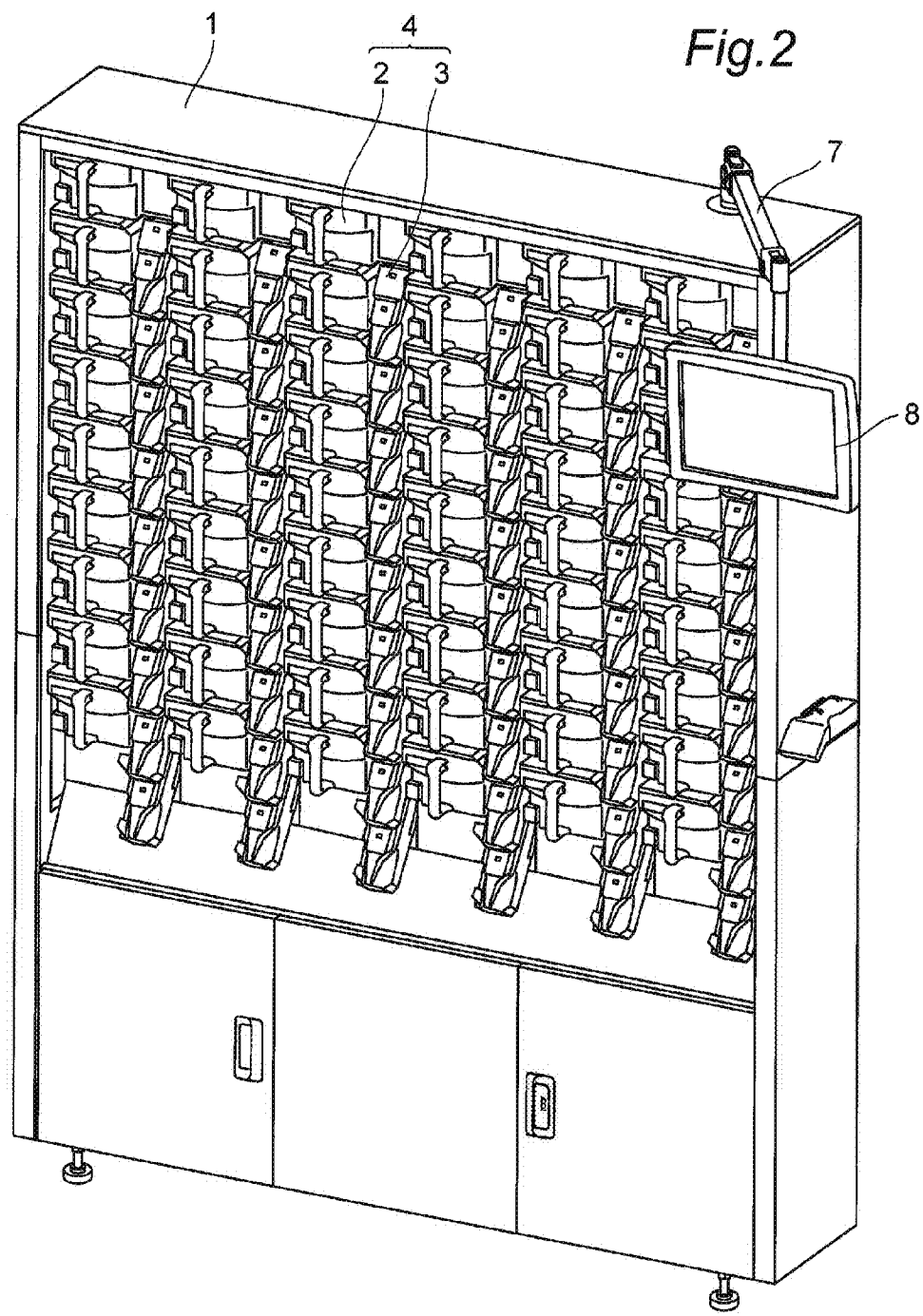
FIG. 2 is a perspective view of the tablet feeder according to the present embodiment.

FIGS. 1 and 2 show a tablet feeder according to the present embodiment. The tablet feeder comprises a device body 1. A plurality of dispensing units 4 are disposed on one face of the device body 1 in vertical and horizontal rows. Each dispensing unit 4 comprises a tablet cassette 2 and a chute 3, wherein each chute 3 is disposed adjacent to a corresponding tablet cassette 2 and is in communication with the corresponding tablet cassette 2. Each tablet cassette 2 is capable of accommodating a plurality of types of tablets and dispenses the tablets contained therein in a lateral direction. A control unit 5 controls such processes as the dispensing of the tablets from the tablet cassette 2. The tablets discharged from the tablet cassette 2 accumulate and are retained in the corresponding chute 3. The chute 3 dispenses the tablets in a downward direction, such that they are manually collected in the tablet container 6. The tablet container 6 used here is made of synthetic resin and comprises a closed bottom, a tubular body, and a flange formed at the outer periphery near the upper opening edge of the container 6. While the container 6 depicted in FIGS. 1 and 2 has a circular cross section, it will be understood by those skilled in the art that the container may have any appropriate shapes, such as a rectangular, hexagonal or other polygonal cross section. Further, it will be understood by those skilled in the art that the tablet container 6 may be made of any appropriate material and may be any appropriate size, depending on the size and number of tablets to be accommodated.

The device body 1 has a roughly rectangular shape and the dispensing units 4 are detachably arranged in vertical and horizontal rows. The tablet cassettes 2 and chutes 3 are arranged vertically, with shifted horizontal positions. Thus, the tablet cassettes 2 are disposed with virtually no gaps therebetween in the vertical direction. The chutes 3 are configured so as to project obliquely forward and downwardly away from the one face of the device body 1. The chutes 3 are positioned such that the lower portion of one chute 3 overlaps with the upper portion of the chute 3 that is positioned immediately below it. With such an overall configuration, when tablets are dispensed from a top chute 3, the lower chute 3, positioned immediately below the top chute 3, serves as a guide for placement of the tablet container 6 into which tablets are dispensed from the top chute 3. Further, the device body 1 is provided with an arm 7 on the top surface thereof and the leading end of the arm 7 is provided with a liquid crystal monitor 8.

Figure 3:
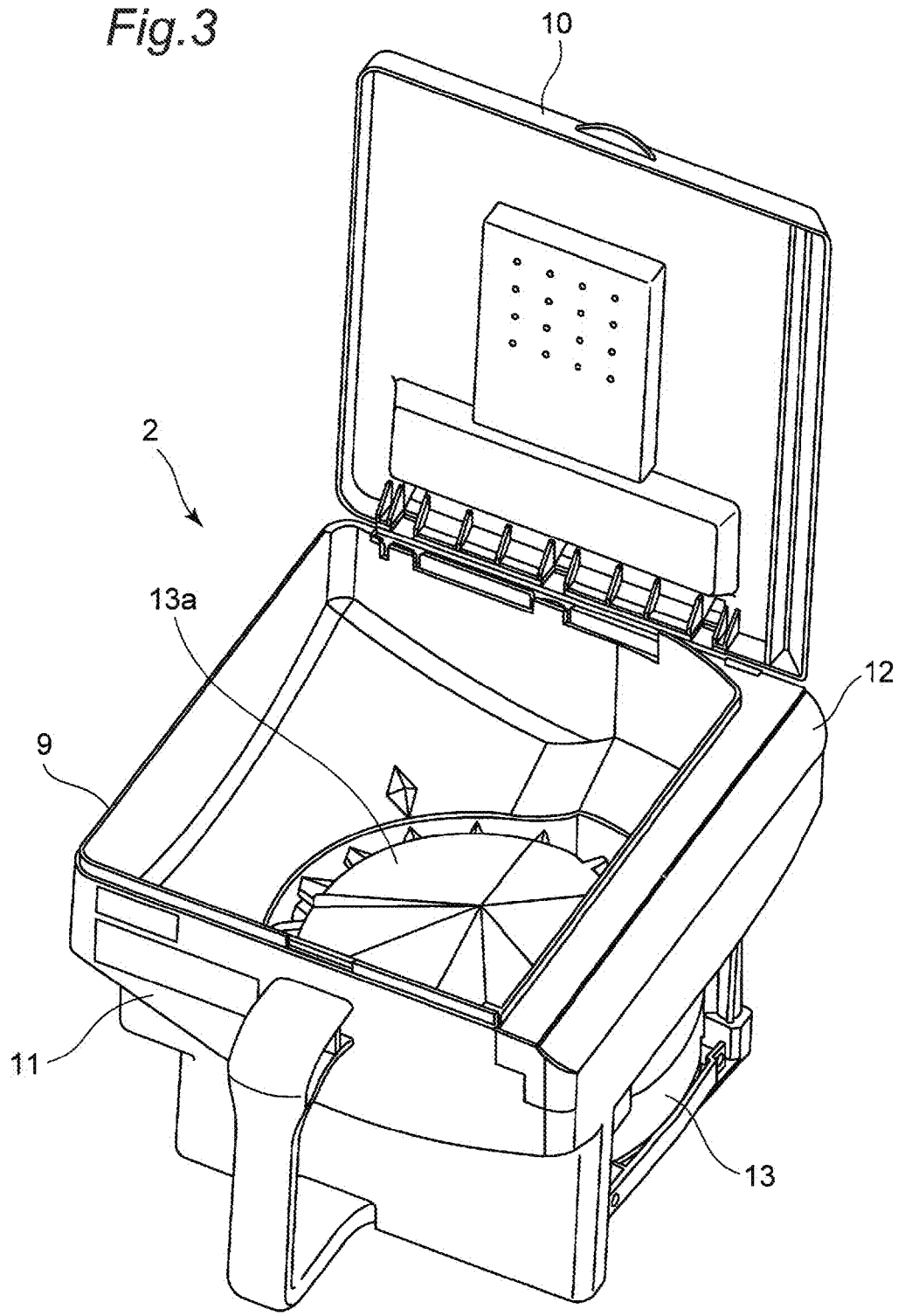
FIG. 3 is a perspective view of the tablet cassette of FIG. 1.
Figure 4:
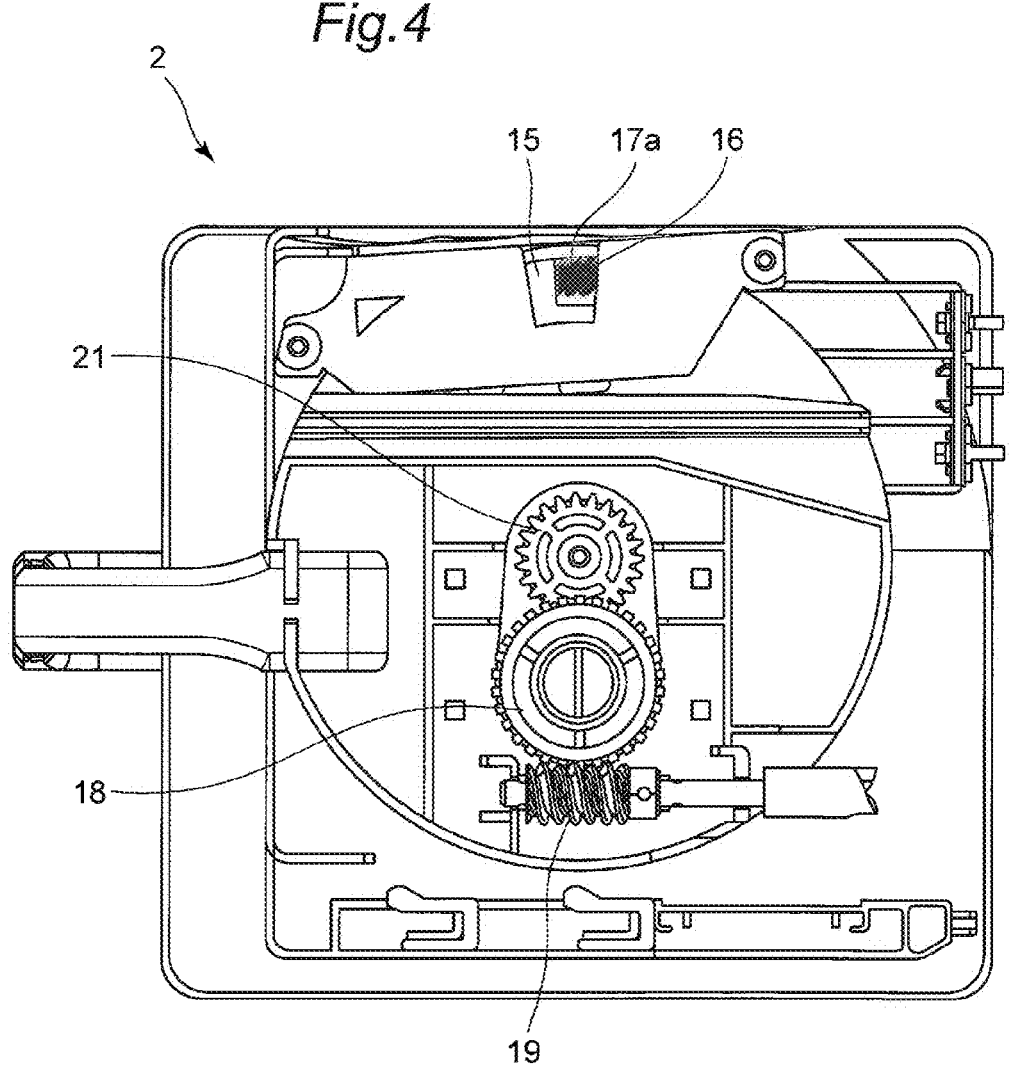
FIG. 4 is a bottom view of the tablet cassette of FIG. 1.
Figure 5:
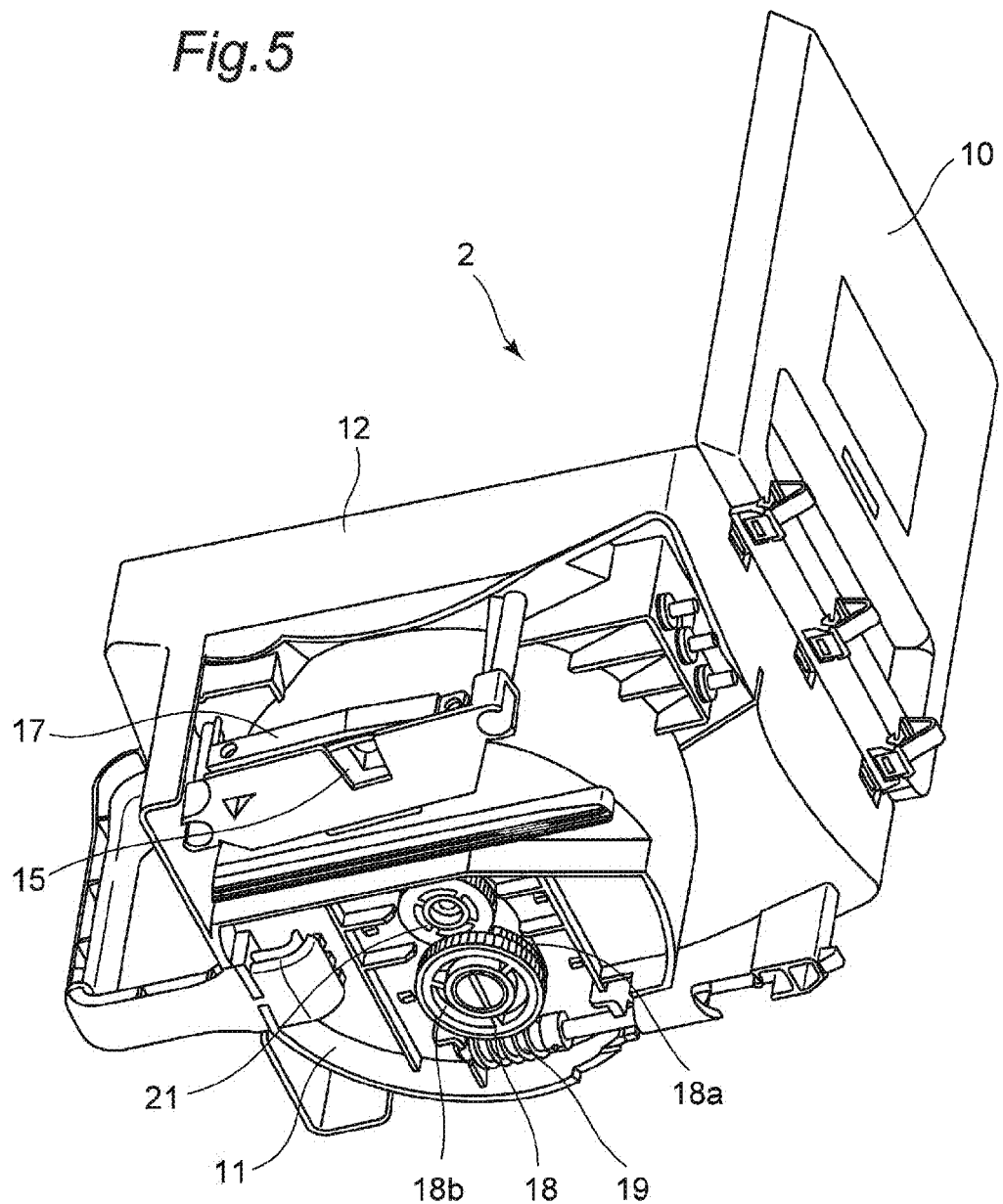
FIG. 5 is a perspective view seen from the bottom side of the tablet cassette of FIG. 1.
Figure 5A:
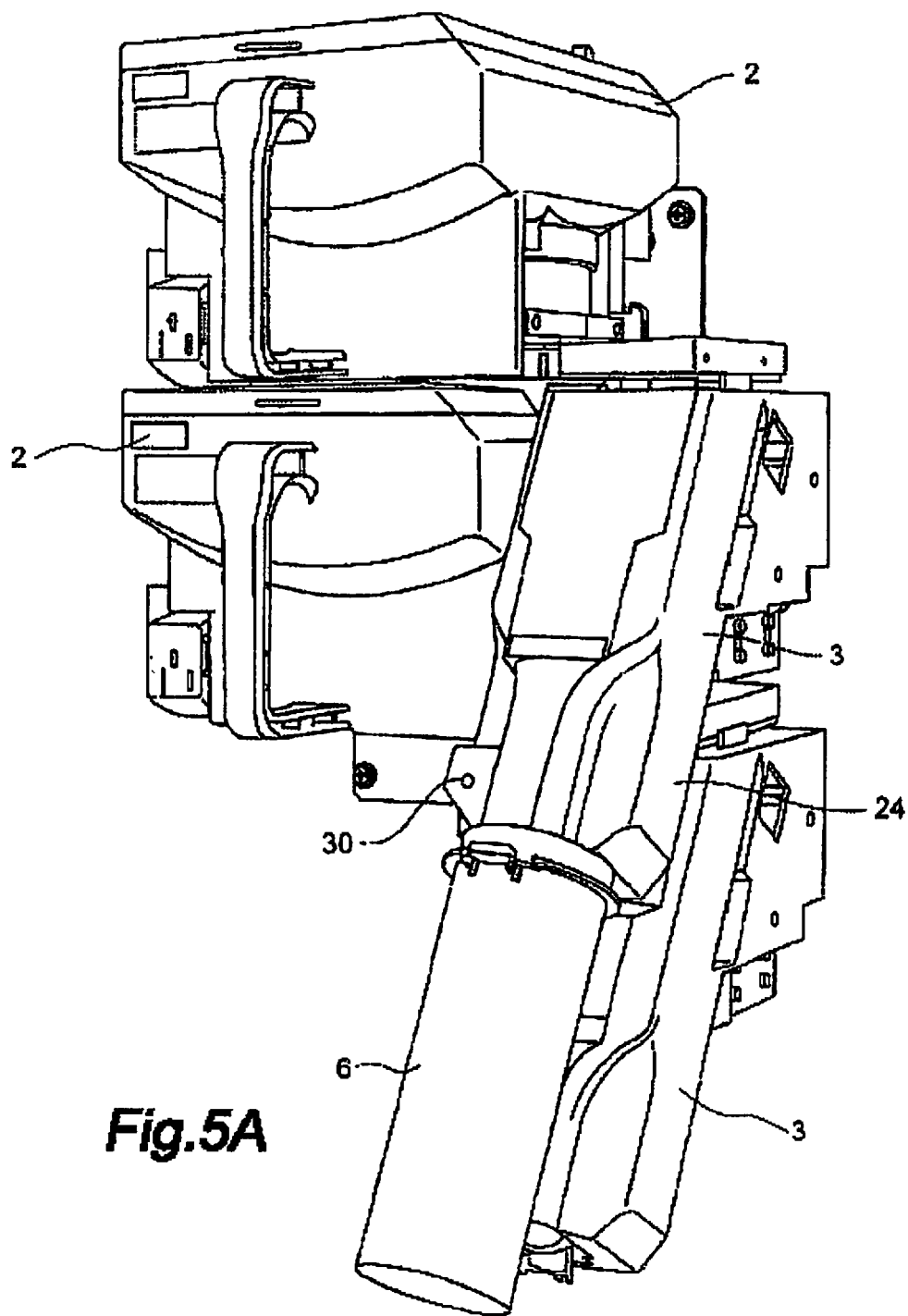
FIG. 5A is a perspective view of two sets of the tablet cassette and chute of FIG. 1.
Figure 6:
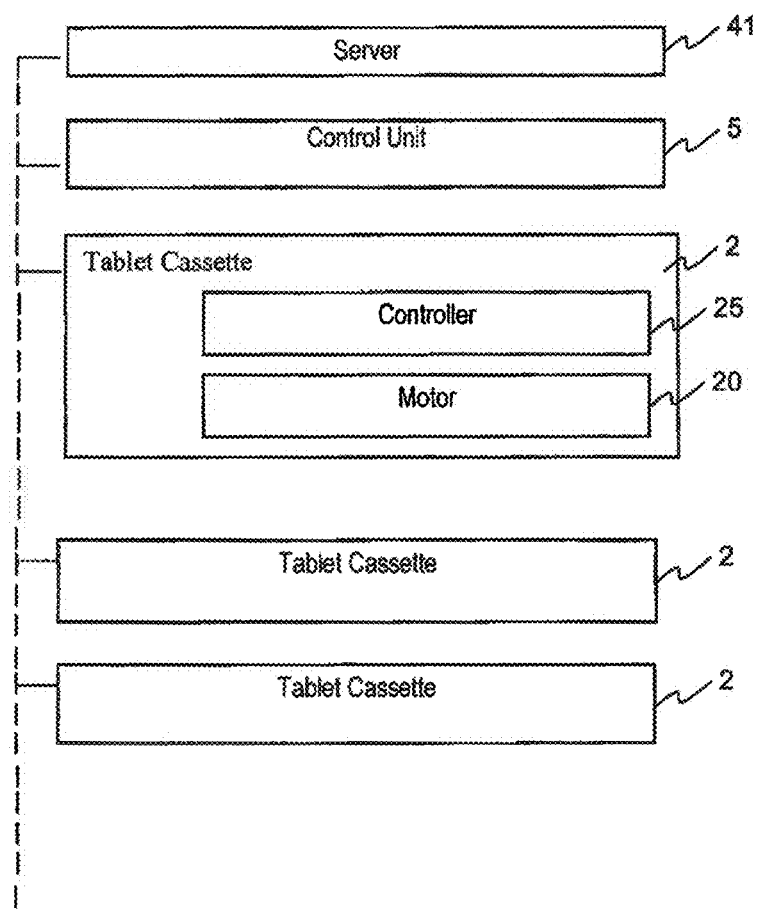
FIG. 6 is a block diagram of the tablet feeder according to the present embodiment.
Figure 7:
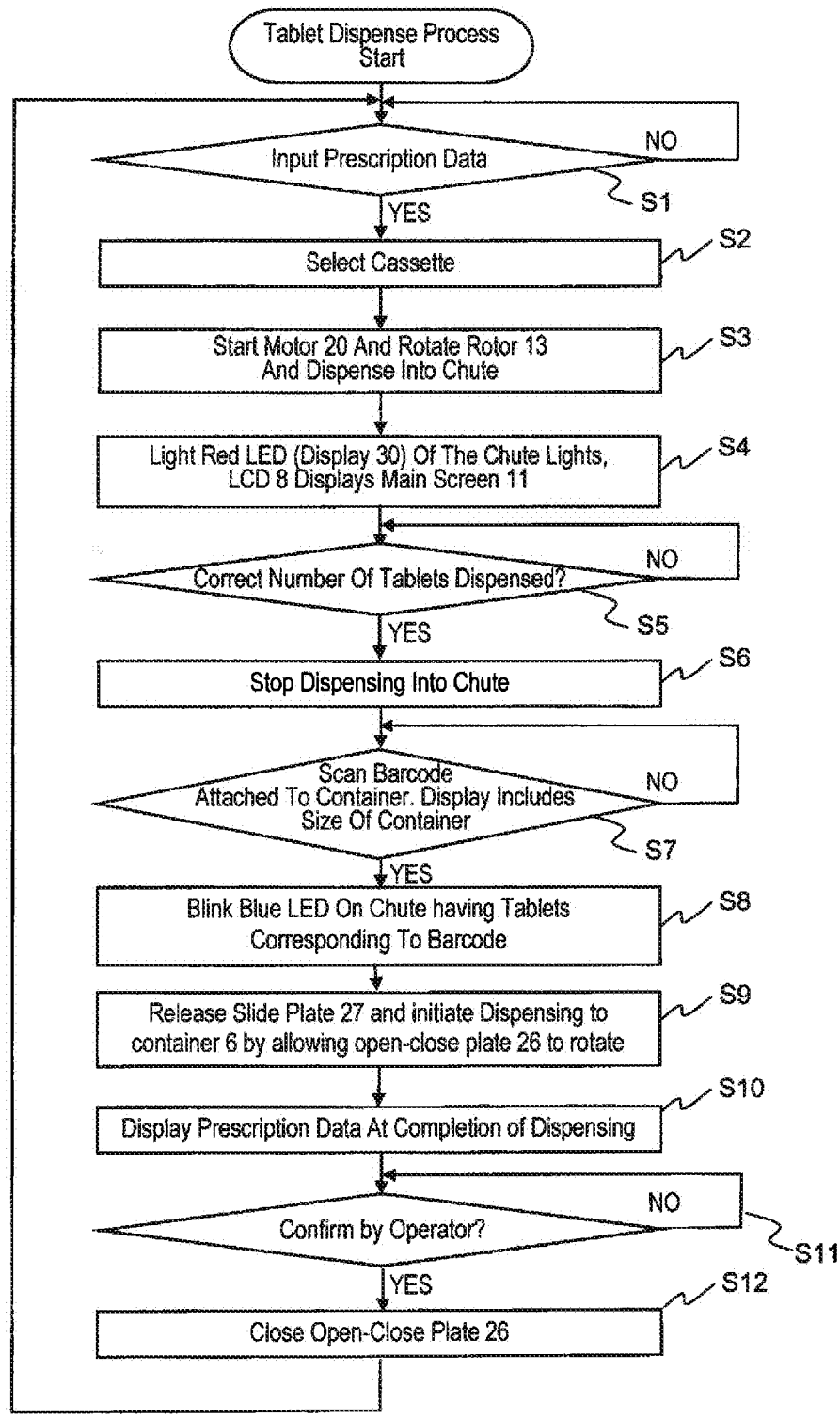
FIG. 7 is a flowchart describing the dispensing process according to the present embodiment.

The liquid crystal monitor 8 comprises a touch panel and display screen, which displays a main screen at start up, as shown in FIG. 7. The main screen displays cassette information, including cassette number, medicine name, indicator and the like, for each tablet cassette 2 provided in the device body 1. An indicator can be configured, for example, from a display unit (not shown) that emits light in three different colors. In cases where the same type of tablet is included in a plurality of prescription data, the indicator lights up to indicate that there will be a subsequent dispensing process; more specifically, the display can be configured to light up in two places when there are two waiting prescriptions, As shown in FIGS. 3 through 5, the tablet cassette 2 comprises a cassette body 9 having an open-close lid 10. Each tablet cassette 2 accommodates a large number of a certain type of tablet. If certain tablets are dispensed more often than others, those medicines may be accommodated in more than one tablet cassette 2. Each tablet cassette 2 can be attached to and detached from the support table of the device body 1. However, when a tablet cassette 2 is attached to the device body 1, it cannot be freely removed therefrom due to a lock mechanism (not shown).

Each cassette body 9 comprises a tubular rotor accommodation part 11 and a tablet accommodation part 12 positioned above the rotor accommodation part 11 and having a generally rectangular shape. The tablet accommodation part 12 has a space formed by the lateral walls and the upper surface (conical surface 13a) of a rotor 13, and is capable of accommodating tablets.

The rotor accommodation part 11 has a tablet outlet 15 (see FIG. 5) and a slit 16 formed on a lateral portion thereof. A separating member 17 is fixed in the vicinity of the slit 16 and a brush part 17a of the separating member 17 projects through the slit 16 into the rotor accommodation part 11.

Further, the rotor accommodation part 11 has an aperture (not shown) in the center of the bottom surface and an intermediate gear 18 rotatably attached around the aperture. The intermediate gear 18 is structured such that a first gear 18a and second gear 18b are integrally provided in a row in the axial direction.

A worm gear 19 is attached to the bottom surface of the tubular rotor accommodation part 11 and engages with the second gear 18b of the intermediate gear 18. The drive force from a motor 20 is transmitted via the worm gear 19 to the intermediate gear 18 so as to rotate the rotor 13.

The rotor 13 has a cylindrical shape and includes a conical surface 13a, the upper surface of which projects toward the center of the rotor 13. An axially extending guide groove (not shown), formed on the outer periphery surface of the rotor 13, accommodates tablets in a vertical and orderly manner. The tablets in the guide groove are vertically separated by the brush part 17a of the separating member 17, such that only the one tablet below the brush part 17a drops through the tablet outlet 15. A rotary shaft is integral with the rotor 13 and provided at a center portion of the bottom surface of the rotor 13. Specifically, the rotary shaft passes through the aperture formed in the bottom surface of the rotor accommodation part 11. A driven gear 21 is fixed to the projecting portion of the rotary shaft. The driven gear 21 engages with the first gear 18a of the intermediate gear 18, such that when the worm gear 19 rotates, the driven gear 21 and rotor 13 rotate via the intermediate gear 18.

The control unit 5 uses prescription data that is input from a server 49 or the like as the basis for executing a series of tablet dispensing processes, such as driving and controlling the relevant tablet cassette 2 to cause tablets to be dispensed into the chute 3, as described below.

Next, the operation of a tablet feeder having the above configuration will be explained according to the flowchart shown in FIG. 7.

When prescription data is input from a server or the like (not shown) (step S1), the tablet cassette 2 holding the desired prescriptive is identified based on such (step S2). According to the process represented by FIG. 7, the prescription data is automatically input. However, the prescription data may alternatively be manually input by an operator using a manual input screen as shown in FIG. 11.

Then, the motor 20 of the identified tablet cassette 2 is driven and the rotor 13 is rotated, initiating a tablet dispensing operation (step S3). At this time, the red LED of display 30 of the chute 3, corresponding to the tablet cassette 2 storing the desired tablets, lights up (step S4) to indicate to the operator that the desired type and number of tablets are being dispensed into the chute 3. Further, the liquid crystal monitor 8 displays the main screen 41 as shown in FIG. 8. The main screen 41 is composed of a plenty of cassette columns 41a which display the layout of the cassettes 2 and are placed as matrix-like, and several kinds of buttons positioned at the lower side of them. The display form of the cassette columns 41a (background color, color of display character, etc.) is changed in response to the state of the tablet cassette 2. Herein, a frame portion of background is displayed as blue color, the cassette number is displayed therein and the medicine name is shown in the middle of it.

When the number of tablets dispensed into the chute 3 is equivalent to the number of tablets specified in the input prescription data (step S5), the motor 20 is switched off and the tablet dispensing operation ceases (step S6). The red LED remains lit at this point. Moreover, in the event that missing part of medicine is occurred during dispensing operation, a frame portion of the cassette column 41a is changed to red color display. In the event that the prescription is canceled, the character of the medicine name is changed to red color in the state of maintaining the frame portion as blue color. In addition, the display form is changed such that a user can discriminate in the case of prescription error, prescription cancel, unregistered medicine, unattached cassette and the like. Thus, a user can recognize the state of each cassette 2 at a glance and the workability can be advanced.

Figure 19:
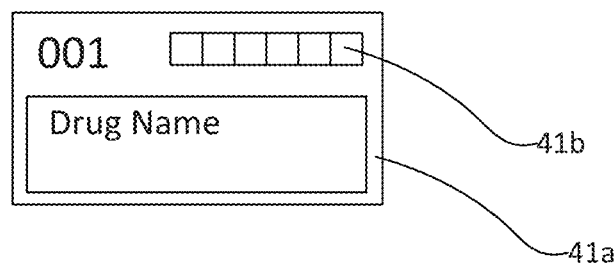
FIG. 19 shows a cassette column displayed in the main screen of FIG. 8.

Further, in the event that a next prescription date including tablets which should be dispensed from the chute 3 is inputted (waiting prescription) before the tablets dispensed from the chute 3 are collected from the tablet cassette 2 into the tablet container 6 based on the prescription data, the display of the cassette column 41a is changed as follows. That is, the indicator (here, five square blanks arranged in a lateral direction) is displayed. While a next prescription data is temporarily memorized in the memory portion of the control unit 5, the indicator 41b displayed on the cassette column 41a (see FIG. 19) of the main screen 41 (see FIG. 8) in the liquid crystal monitor 8 is blinked. Herein, the first blank of the five is blinked (for example, as green), so as to inform that the first prescription is in the waiting state. Furthermore, if there is a next prescription, the second blank may be blinked and it becomes possible to deal with a waiting data of maximum five descriptions (in this case, a description data is temporally memorized in the memory portion in series.

Figure 20:
FIG. 20 shows a priority determined column displayed on the liquid crystal monitor of FIG. 1.

In the case that tablets included in a plenty of waiting prescriptions are accommodated in one chute 3, it is possible to dispense the tablets in accordance with the predetermined priority order. For example, it is possible to display the priority determination column shown in FIG. 20 and set the priority rank of a prescription data (here, five steps). Thus, in the case that there are a plenty of waiting prescriptions to a chute 3, it is possible to dispense tablets which should be dispensed in first according to the priority order despite its waiting order.

In addition, the indicator can be utilized during the division prescription as described below.

Figure 9:
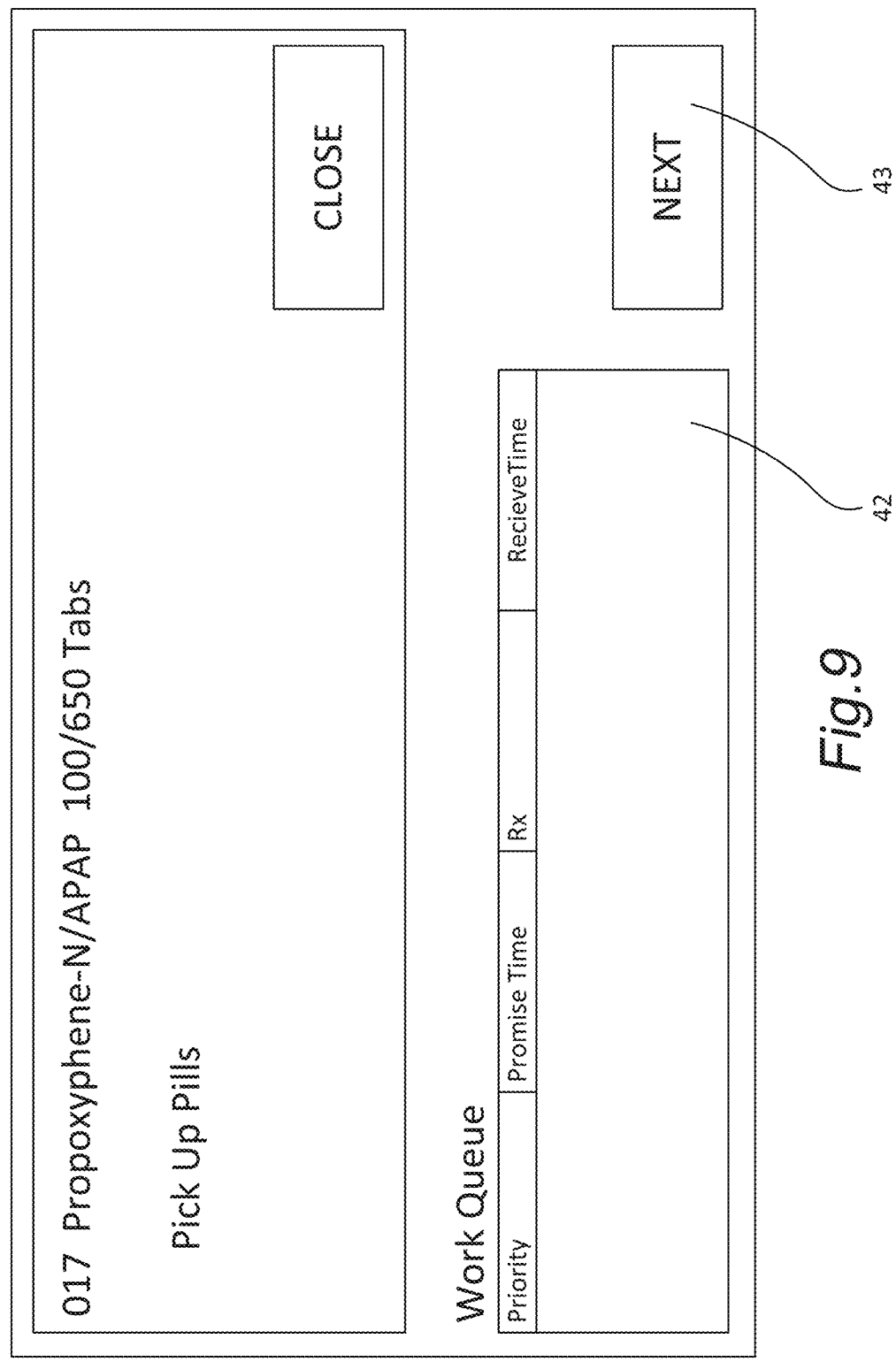
FIG. 9 shows an information screen displayed as a popup on the main screen of FIG. 8.

A barcode is developed in accordance with the prescription data and disposed on the tablet container into which the desired tablets are to be dispensed. After the desired tablets have been dispensed into the chute 3, the barcode is scanned by a barcode scanner (step S7) and the blue LED of display 30 of the chute 3 in which the desired tablets are accumulated begins to blink (step S8). Thus, the operator can tell at a glance from which chute 3 the tablets will be dispensed. Further, at this point, a solenoid is driven, such that engagement part 40 and engagement receiver 38 of the slide plate 27 are released from engagement (step S9). Thus, movement of the gate plate 26 becomes possible. The liquid crystal monitor 8 displays a pop-up information screen as shown in FIG. 9. Preferably, the information screen displays the suitable size of the tablet container 6 to be used, as calculated based on the number of the tablets to be dispensed from the tablet cassette 2 to the chute 3. For example, the information screen may state "40DR is the best!" In another possible configuration, when the prescription data of a plurality of succeeding prescriptions is input, such that there are prescriptions waiting to be dispensed from tablet cassettes 2, the waiting prescription data is displayed in a "Work Queue" column 43, such that an operator can switch the order of the operation by a "Next" button 42.

Next, the operation of dispensing the tablets from the chute 3 to the tablet container 6 may be initiated. Because the guide path 24 has a translucent front surface and is provided with lines indicating volume, the operator can determine at a glance whether the tablet container 6 is suitable for all of the tablets in the chute 3 that are to be dispensed. Accordingly, an operator need not worry about using the wrong size tablet container 6.

During the tablet dispensing operation, an operator positions the tablet container 6 against the pressure receiver 33 of the chute 3 with the blinking blue LED (display unit 30), such that the open end of the tablet container 6 abuts the pressure receiver 33. In this position, the locking nail 34 abuts the outer periphery surface of the tablet container 6 and the slip prevention part 35 abuts the flange. Thus, even when the tablet container 6 is pushed against the pressure receiver 33, the tablet container 6 is not displaced. Further, as the pressure receiver 33 is pushed against by the tablet container 6, the gate plate 26 rotates around the pivot 31, such that the lower end opening of the guide path 24 gradually becomes exposed. The guide pin 26a also moves in the guide groove 24a in conjunction with the rotation of the gate plate 26. Thus, without changing the direction or orientation of the force applied upon the pressure receiver 33, the position of the open end of the tablet container 6 moves in a direction parallel to the open end of the guide path 24. As such, the dispensed tablets are smoothly accommodated in the tablet container 6 without falling out or spilling. Further, the pivot 31 moves along the guide groove 32, and the slide plate 27 moves in an upward direction in conjunction with movement of the gate plate 26. Thus, any tablets accumulated in the chute 3 or guide patch 24 and jammed or stuck toward the upper part thereof are forcibly jarred by the slide plate 27, such that the tablets become free to move through the chute 3 to be dispensed into the tablet container 6 from the guide path 24. When the container locking part 24b provided at the lower end of the guide path 24 comes into contact with the inner surface of the open end of the tablet container 6, the rotation of the gate plate 26 is inhibited, and a degree of exposure of the area defining the opening of the tablet container 6 is obtained. In other words, a degree of the exposure of the opening of the guide path 24 or chute 3 corresponds to the size of the open end of the tablet container 6, preventing the problem of tablets falling out and also tablets are dispensed into the tablet container 6 at one time.

When the dispensing of the tablets from the chute 3 to the tablet container 6 is thus completed, the liquid crystal monitor 8 displays the prescription data of the dispensed tablets (step S10). For example, the prescription data that is displayed may include patient data or the like. The operator then confirms that the information displayed is correct and performs a confirmation operation, by touch-operating, for example, a "confirmation" button displayed in the liquid crystal monitor 8. Once the confirmation operation is executed (step S11), the solenoid is driven, and the gate plate 26 is locked in the closed position (step S12). By such a procedure, the series of tablet dispensing processes is completed.

(Interruption process)

In the event an interruption process must be performed, whereby prior to the dispensing of the tablets dispensed into and accumulated in a first chute 3 into the tablet container 6, tablets dispensed into and accumulated in a second chute 3 are to be dispensed first, the following steps may be performed. Initially, the barcode on the tablet container 6 into which the tablets from the second chute 3 are to be dispensed is scanned. Then, once the barcode is scanned, the LEDs on the first chute 3 are turned off, the solenoid connected to the first chute 3 is driven, and the gate plate 26 of the first chute 3 is locked so as to be maintained at the closed position. This prevents the possibility of accidentally dispensing the tablets from the first chute into the tablet container 6. However, preferably, in order to reflect that tablets are being dispensed into the first chute 3, a different color LED is lit up, for example, to alert the operator.

(Troubleshooting)

In the event that tablets become jammed in a tablet cassette 2 or have run out during the tablet dispensing operation, the liquid crystal monitor 8 identifies the jammed or depleted tablet cassette 2 or the LEDs provided on the relevant tablet cassette 2 become lit. For example, the background of the liquid crystal monitor 8 may be displayed in red to facilitate identification of the relevant tablet cassette 2. In this case, it is preferable that the method by which an operator is alerted of jamming of tablet in a tablet cassette 2 is different from the method by which an operator is alerted of a tablet cassette 2 that has run out of tablets. Further, a tablet jam can be detected based on the state of conduction to the motor 20 or the rotating state of the output shaft of the motor 20 and so on, while a lack of tablets can be detected based on the detection signal from the tablet detection sensor. This allows the operator to immediately identify the tablet cassette 2 in question and address the problem. Alternatively, through touch operation of the area on the liquid crystal monitor 8 for the relevant tablet cassette 2, the dispensing information screen, as shown in FIG. 10 is displayed. The dispensing information screen then displays a "reset" button 43 or the like so that the necessary processes are performed.

(Prescription Cancel)

In the event that a tablet dispensing operation is cancelled midway through the dispensing process, such as when a signal to cancel a prescription is input, the rotation of the rotor 13 is stopped, and the LEDs on the chute 3 in which the tablets to be dispensed have accumulated become illuminated. In the same manner as above, the operator can then dispense any accumulated tablets from the chute 3 into the tablet container 6. Next, the liquid crystal monitor 8 displays a "completion" button, showing that the prescription cancel has been completed and, through touch operation of this button, the prescription cancel process may be completed, (Consecutive Dispensing of the Same Type Tablets)

In cases where the same type of tablets is to be consecutively dispensed, tablets cannot be dispensed from a tablet cassette 2 into a chute 3 if the tablets previously dispensed from the tablet cassette 2 have accumulated in the chute 3. Thus, the operation of the tablet cassette 2 is suspended until the tablets are dispensed from the chute 3 to the tablet container 6, and the liquid crystal monitor 8 displays that such an effect has taken place. In this case, preferably the liquid crystal monitor 8 indicates certain information, such as a notice that tablet dispensing from that particular tablet cassette 2 is in a standby state, as well as other information such as number of tablets being dispensed. Thus, the possibility of mistakenly dispensing the tablets into a different tablet container 6 is prevented.

(Tablet Collecting Process)

In the event that electric power is not supplied because of power outage, etc. and the device is stopped, tablet collecting process is performed as follows.

Tablets are dispensed into each chute 3 based on the inputted prescription data. Thus, when the device is stopped in this state, the data in the device side about the dispensed tablets is lost although the tablets have already dispensed into the chute 3. This makes the device impossible to continue the process from the state before it is stopped after power supply is returned.

Figure 21:
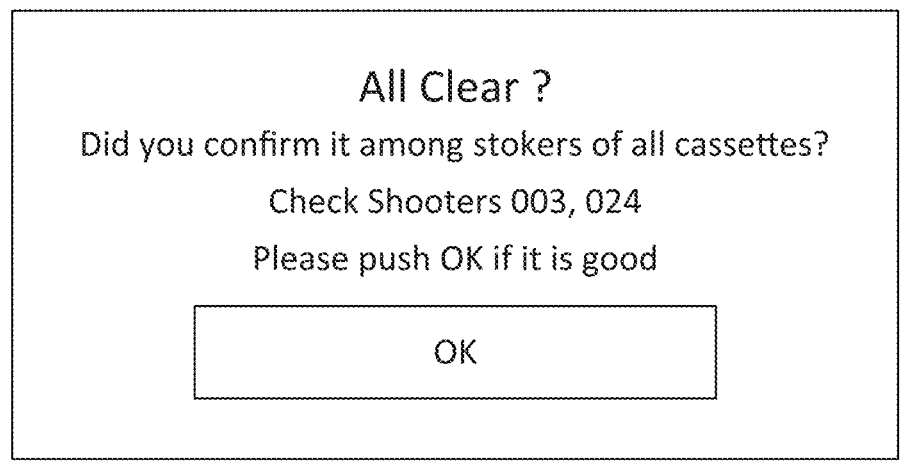
FIG. 21 is an initialization completed screen displayed on the liquid crystal monitor of FIG. 1 and shows the state which a tablet cassette is remained in the chute.

In this case, it is needed to collect the tablets which have already dispensed into each chute 3 manually. Initialization required screen is displayed on the liquid crystal monitor 8. When an initialization button is touched, the locked state of all chutes 3 is removed and the screen is changed to initialization completion screen. Tablets dispensed from the chute 3 are collected. When collecting operation is finished and OK button is touched on the initialization completion screen, the tablet collecting process is finished. However, in the case that tablets dispensed to the chute 3 are remained, alarm is displayed on the initialization completion screen. As shown in FIG. 21, the background of the cassette column 41a corresponding to the chute 3 having remained tablets is displayed as red. Moreover, the LED of each chute 3 is blinked. This makes a user possible to easily judge which chute 3 has tablets remained at a glance.

As seen above, even when the device it turned from the stop due to power interruption, it is possible to judge which chute 3 has tablets remained at a glance, such that the collecting process of tablets can be easily performed. Thus, tablets are not maintained to remain in the chute 3. Restart of the device can be smoothly performed. When tablets prescribed after that are dispensed, the occurrence of trouble, quantity error, etc. are prevented.

(Recommended Bottle Size Display Process)

Figure 22:
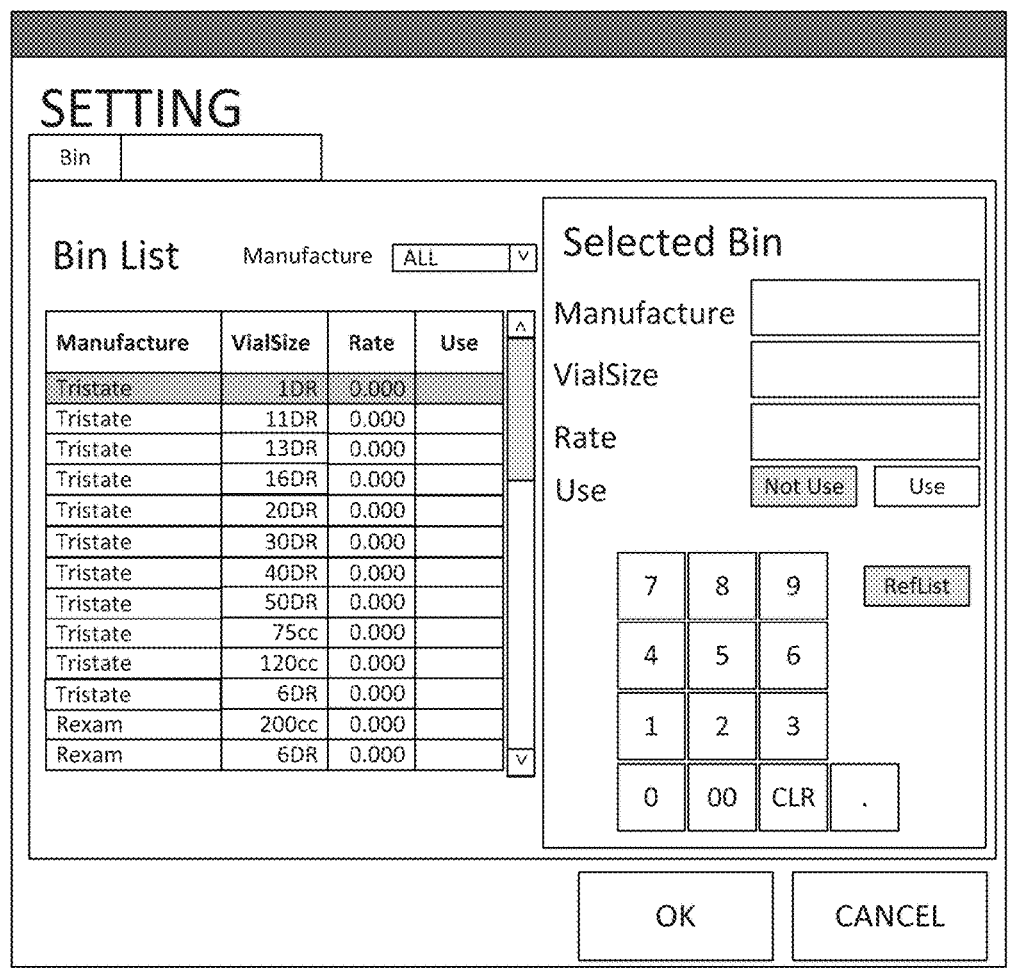
FIG. 22 is a list chart which is memorized in the memory of the control unit of FIG. 6 and shows the ratio of maximum number of tablets to be accommodated in the vial bottle.

The maximum number of tablets which can be respectively accommodated in each size of tablet containers 6 (vial bottles) used in the device is memorized in the memory of the control unit 5. For example, in the list shown in FIG. 22, in the case that the maximum number of tablets A which can be accommodated in the vial bottle which size is 20DR is 100 tablets, the rate is determined at 1 and the 20DR vial bottle becomes a standard tablet container. A 30DR vial bottle is memorized that rate is 1.5 and the maximum number of tablets is 150 against the 20DR vial bottle. A 40DR vial bottle is memorized that rate is 2 and the maximum number of tablets is 200, A vial bottle to be dispensed is determined according to the dispensed number of a tablet (for example, tablet A) included in the prescription data as follows. That is, the range of tablet number to be accommodated is divided in order from the minimum size of vial bottle and each range is related to each size of a vial bottle. The size of a vial bottle is determined which range the dispensing number belongs to. Specifically, in the said example, when the dispensing number N is N<100, the determined size of the vial bottle is 20DR, and N is 100≤N<150, size is 30DR, and N is 150≤200, size is 40DR. The determined size of the recommended bottle is displayed on the liquid crystal monitor 8. Thus, a user may prepare the corresponding vial bottle according to the size which is automatically determined based on the prescription data and displayed. As a result of this, he or she can promote the dispensing operation of tablets efficiently. In addition, when the dispensing number is over 200 tablets, it is possible to inform error or perform the division process as described below. With respect to another tablet, tablet B or C, etc. which is different kind from tablet A, the maximum number of tablets which can be accommodated in the 20DR tablet container 6 or the ratio to the maximum number of tablets A may be memorized. In the case of the latter, a vial bottle is determined in accordance with the ratio memorized. Furthermore, when there is no stock of the vial bottle having the corresponding size, one larger size vial bottle can be automatically selected based on the stock information, (Shop Adoption Bottle Registration Process)

A maker or size of a vial bottle which a shop adopts is different. However, to register the maximum number of all kind of tablets respectively about each several size vial bottle of each maker is problem such that it is required great care because of the enormous number. In the case that a vial bottle or a tablet is newly registered, the same problem is occurred. Thus, the maximum number of tablets to the standard tablet container is memorized in master data. With respect to another vial bottle (not only the different size vial bottle of a same maker, but also several size vial bottle of other makers), the ratio of each vial bottle against this value is memorized. The maximum number of the other vial bottles is calculated by multiplying the maximum number of tablets of the standard tablet container by the ratio in accordance with the kind of tablet to be accommodated. This eliminates the need for memorizing the maximum number of each tablet to the other vial bottle and can omit troublesome time and effort to register and further can flexibly respond to a vial bottle or tablet registered newly.

(Division Prescription Process)

In the case that all dispensing number of a tablet included in a prescription data is not accommodated in a vial bottle although the bottle has the maximum number of tablets in which can be accommodated, the tablets are divisionally prescribed by dividing several vial bottles.

Figure 23:
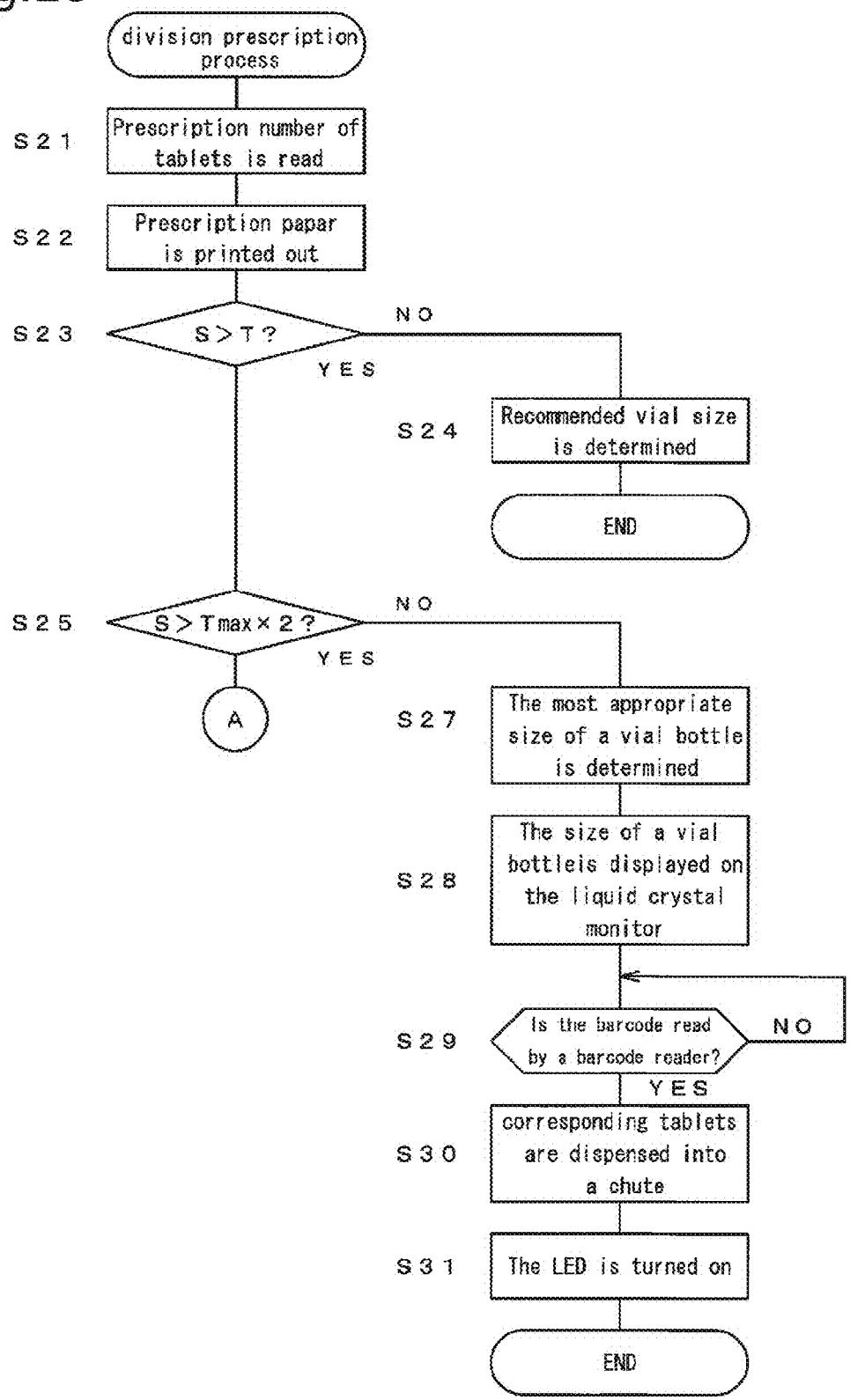
FIG. 23 is a flowchart showing the content of the division prescription process according to the present embodiment.
Figure 24:
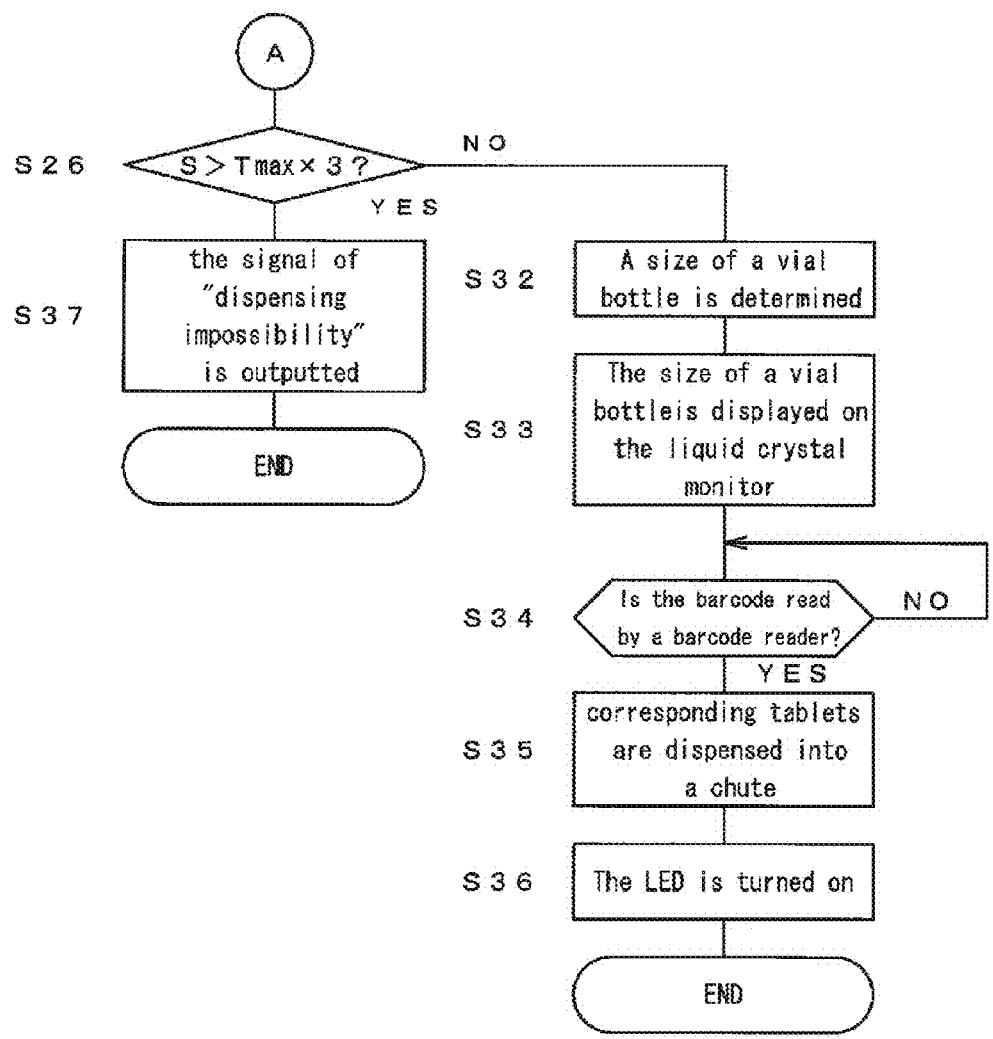
FIG. 24 is a flowchart showing the content of the division prescription process according to the present embodiment.

As shown in flowcharts of FIGS. 23 and 24, firstly, prescription number of tablets (the number of tablets prescribed) is read (step S21) and the prescription paper is printed out (step S22), It is judged whether or not the prescription number S of tablets is more than the tablet number which can be accommodated in the largest vial bottle (step S23). If the prescription number S is less or equal to the maximum number of tablets Tmax, the recommended vial size is determined based on the prescription number in the same manner as the above (step S24). In the event that the prescription number S is over the maximum number of tablets Tmax, it is further judged whether or not the prescription number is more than three times as large as the maximum number of tablets (step S26).

In the event that the prescription number S is less or equal to twice as large as the maximum number of tablets, the most appropriate size of a vial bottle is determined based on the prescription number. Herein, the size of a vial bottle is determined based on the value which is obtained by dividing the prescription number in the same manner as the step S22. If the size of a vial bottle is determined, that effect is displayed on the liquid crystal monitor 8 (step S28). If the barcode printed on the prescription paper is read by a barcode reader (step S29), corresponding tablets are dispensed into a chute 3 (step S30). In this case, if the same tablets are accommodated into several tablet cassettes 2, the tablets may be dispensed from the two of them respectively.

Further, if the same tablets are accommodated in only one tablet cassette 2, firstly, the divided tablet number may be dispensed from it. And, the LED of the chute 3 dispensing tablets is turned on (step S31). In this case, it is preferably to blink the LED twice so as to inform that it is divided into two. Furthermore, if the twice blinking is performed with respect to each predetermined time, a user will not miss it. It is preferably to display such that a user can identify the difference between in the case of dispensing tablets to two points and in the case of dispensing tablets to one point (for example, it is preferably to change a color of the display, etc.). In the case of dispensing tablets to two points, it is only necessary to collect from each chute 3 by using two vial bottles. In the case of dispensing tablets to one point, it is only necessary to dispense a half of the rest tablets to the chute 3 again after it is finished to collect a half of the prescription number of the tablets dispensed from the chute 3. At this time, it is preferably to inform that the operation for collecting a half of the rest tablets is remained by blinking a LED one time (It is preferably to blink a LED with respect to each predetermined time.).

In the case that the prescription number of tablets is less or equal to three times as large as the maximum number of tablets, a size of a vial bottle is determined based on the obtained value as well as the step S27. After a size of a vial bottle is determined, a process similar to the case of dividing tablets into two is performed. In addition, when tablets are dispensed from the same tablets cassette 2 to the chute 3 (in the case of dispensing tablets to one point), the division number may be displayed as the lighting number of an indicator provided on the chute 3. This enables a user to recognize the division number at a glance. The lighting number of the indicator may be decreased at every time when tablets are dispensed into a vial bottle. This enables a user to recognize the rest number of collecting operation into a vial bottle. In addition, when tablets are divided into two or three, blank number corresponding to the division number may be lighted at the indicator of the cassette column 41*a*, In the case that the prescription number is more than three times as large as the maximum number of the accommodated tablets, the signal of "dispensing impossibility" is outputted (step S37), and after a series of process is finished.

This makes it possible to dispense tablets divided into several vial bottles and respond it flexibly even when a lot of tablets are needed to be dispensed since the division prescription is available. Although tablets are divided into three or less in the above example, it is possible to divide tablets into four or more. Furthermore, the division prescription may be utilized to enable tablets to dispense into a vial bottle whose size is small when a part size of vial bottles is missed.

(Other Embodiment)

The present invention is not limited to the configuration disclosed in the above described embodiment, and various modifications are possible.

For example, each chute 70 can be configured as shown in FIGS. 12 through 18.

Figure 13:
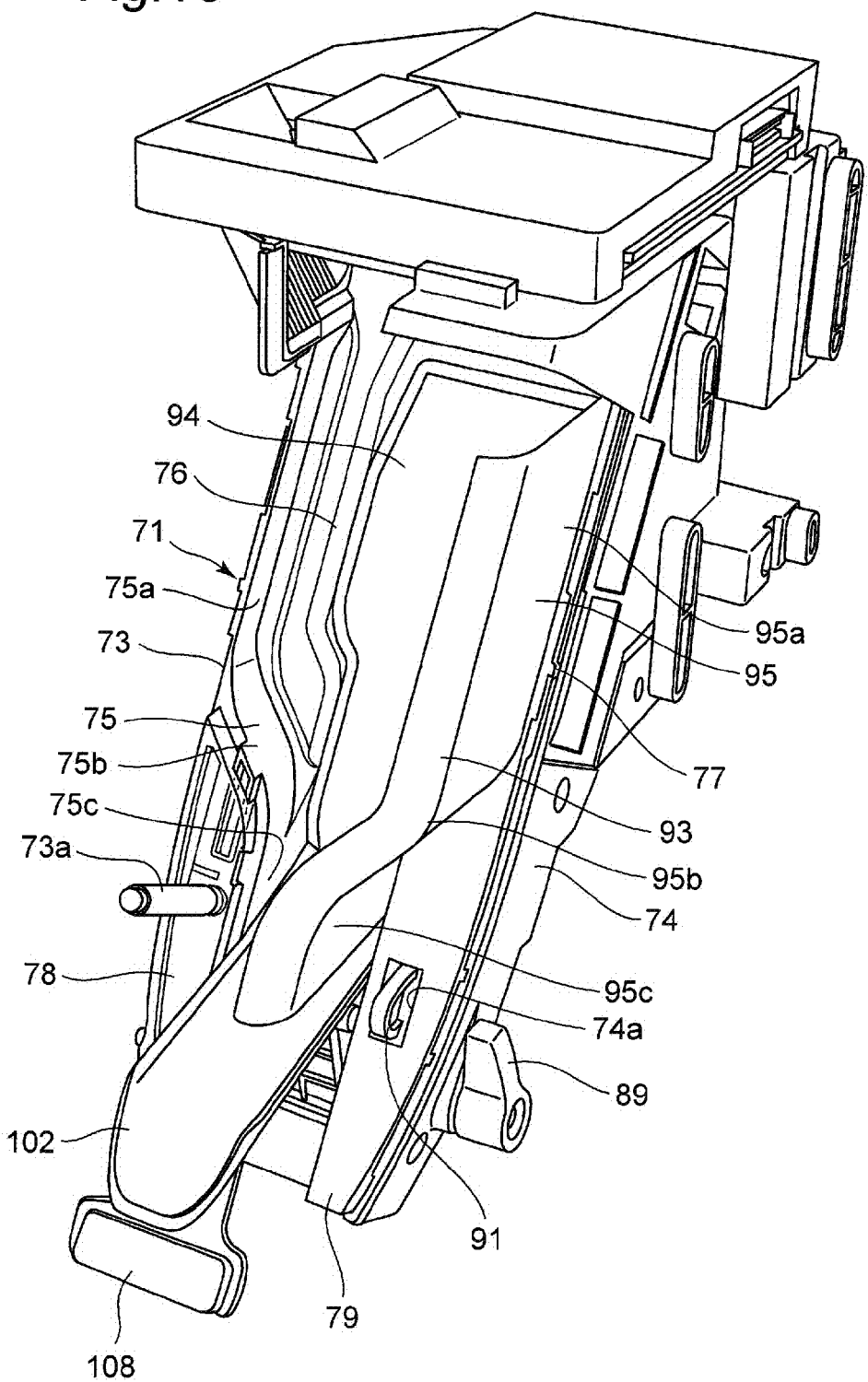
FIG. 13 is a perspective view showing the chute of FIG. 12 with the caver removed.

As shown in FIG. 13, the chute body 71 is composed of a first half portion 73 and a second half portion 74. An interior surface of a side wall of the first half portion 73 is composed of a body side first guide wall 75 gradually expanding from a middle part to inside of it. The body side first guide wall 75 is composed of a series of a first straight line portion 75*a*, a curvature portion 75*b* and a second straight line portion 75*c*. A convex portion 76 is formed in the further inside of the body side first guide wall 75. An inside surface of a side wall of the second half portion 74 is gradually expanded from a middle portion to inside of it and composed of a body side second guide wall 77 guiding the side surface of the slide plate 93. A second auxiliary member 78 is attached to a lower portion of the second half portion 73 respectively.

Figure 17:
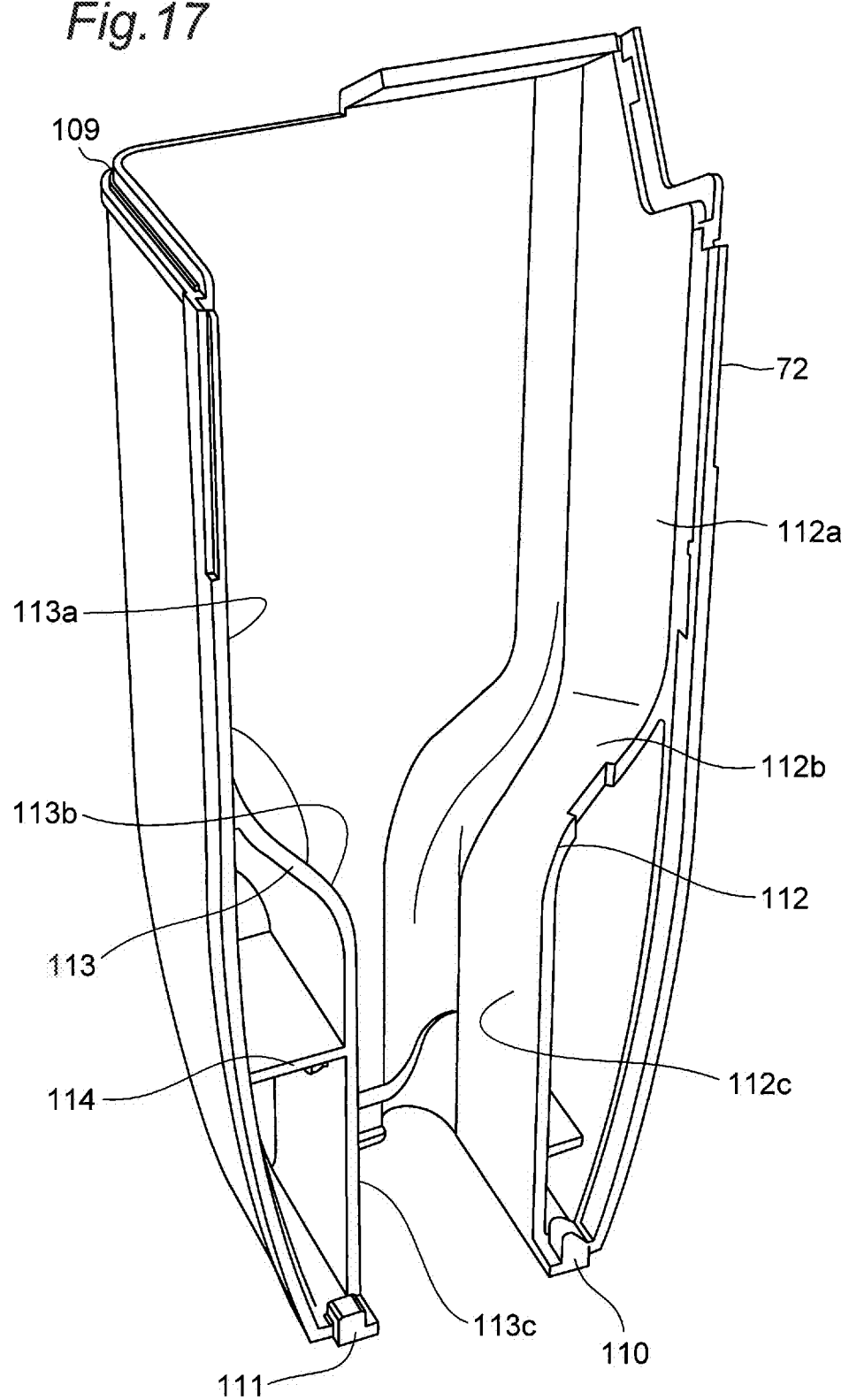
FIG. 17 is a perspective view showing the caver seen from the opposed side of FIG. 12.
Figure 18:
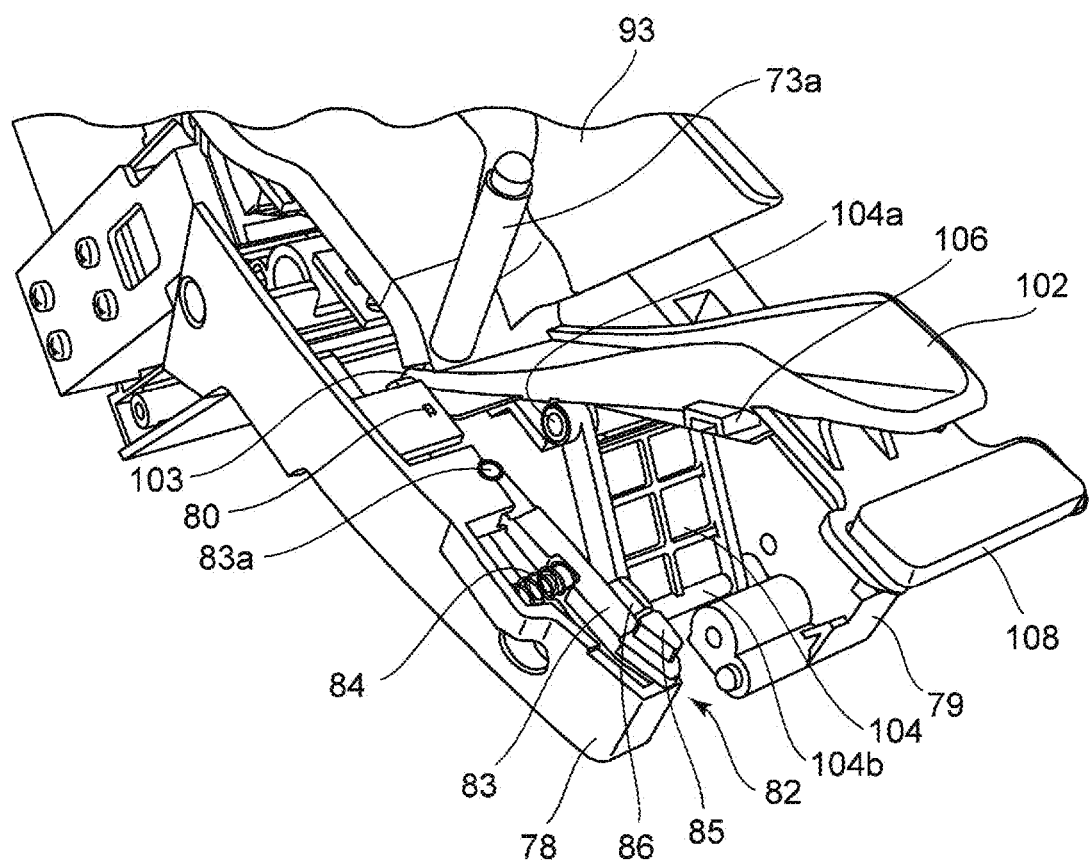
FIG. 18 is a partial perspective view showing the chute of FIG. 12 with the first half portion and the second half portion removed.

As shown in FIG. 18, a LED 80 is placed between the first half portion 73 and the first auxiliary member 78. The LED 80 lights in a state that the cover 72 is attached to the chute body 71 and the lower opening portion of it is closed by a gate plate 102 as described below. Thus, when a dispensing preparation of tablets to the chute 70 is completed, the LED lights. Furthermore, when tablets are dispensed, the LED 80 blinks and it is informed to be able to collect tablets by the tablet container 6 (not shown in FIGS. 12 through 18).

Figure 14:
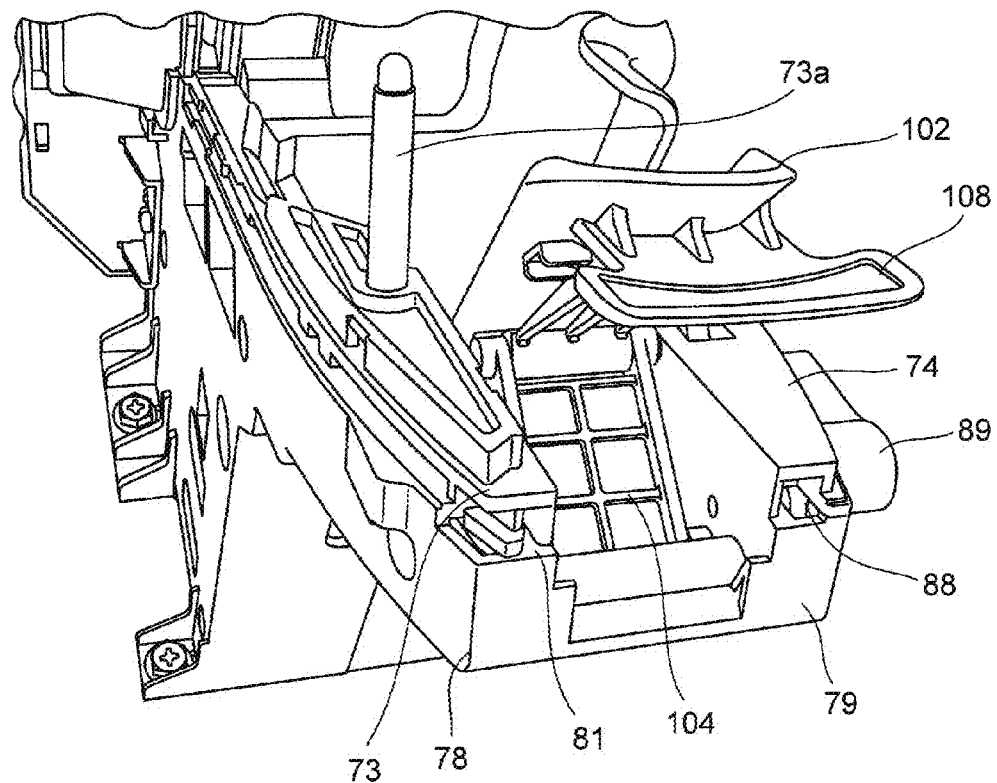
FIG. 14 is an enlarged perspective view of the lower end side of FIG. 13.

As shown in FIG. 14, a first engagement hole 81 is formed in a lower portion composed of the first half portion 73 and the first auxiliary member 78. A lock mechanism 82 is provided in the first engagement hole 81. As shown in FIG. 18, this lock mechanism 82 comprises a rotatable piece 83 provided to pivot around a support axis 83*a* and a coil spring 84 biasing this rotatable piece 83. A click portion 85 is formed at the top of the rotatable piece 83 and a locking projecting portion 86 is formed at the side edge of a middle portion. The click portion 85 is pushed by a first engagement projecting portion 110 (described below) of the cover 72 inserted into the first engagement hole 81. The engagement projecting portion 86 is engage with and detach from an engagement receiver 106 of a gate plate 102 as described below. The coil spring 84 biases the gate plate 102 in the direction to maintain a state that the engagement projecting portion 86 engages the engagement receiver 106. When the cover 72 is attached to the chute body 71 and the click portion 85 is pushed to the first engagement projecting portion 80 so that the rotatable piece 83 rotates against the biasing force of the coil spring 84, the engagement projecting portion 86 is departed from the engagement receiver 106. In addition, a taper surface is formed at the under surface of the tip of the engagement projecting portion 86, so that it smoothly engages with the engagement receiver 106 of the gate plate 102. Furthermore, A axis-like guide portion 73*a* which guides the light from the LED 80 is formed at the front surface of the first half portion 73.

Figure 16:
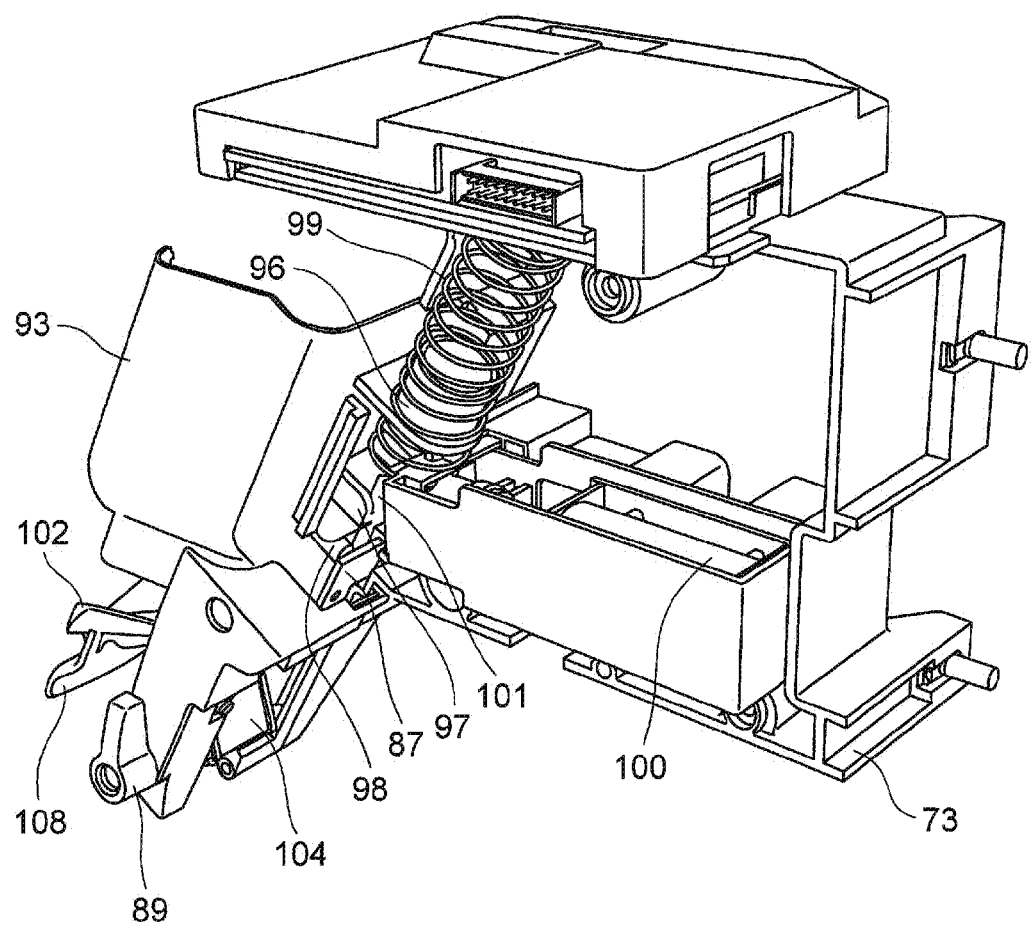
FIG. 16 is a perspective view showing the chute seen from the opposed side of FIG. 14.

As shown in FIG. 16, a detection sensor 87 is provided between the second half portion 74 and the second auxiliary member 79. The detection sensor 87 detects a detected portion 98. The detected result is utilized to judge whether or not the slide plate 93 is positioned at the upper position (the closure position of the gate plate 102).

Figure 15:
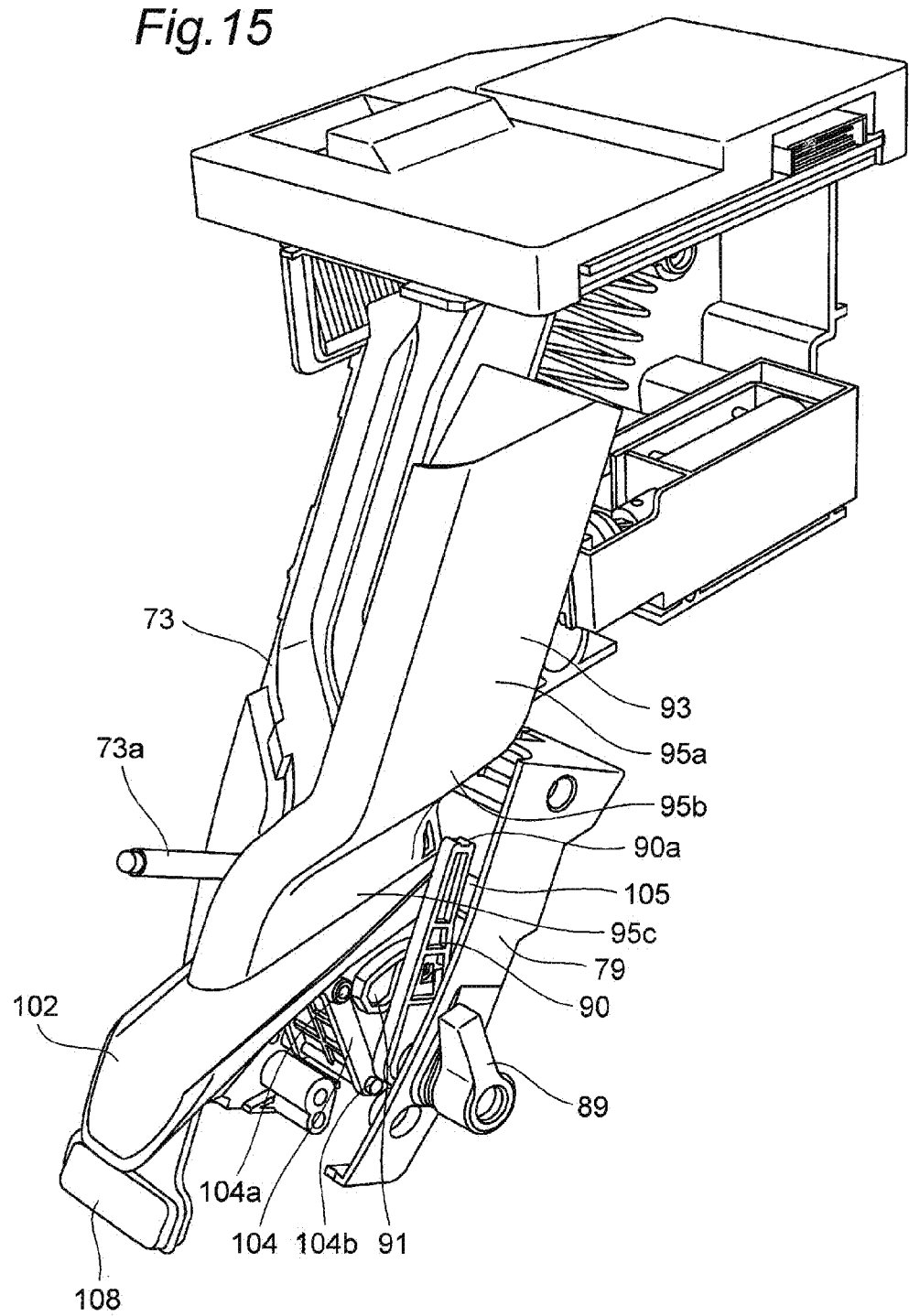
FIG. 15 is a perspective view showing the chute of FIG. 13 with the second half portion removed.

As shown in FIG. 14, a second engagement hole 88 is formed at the lower portion composed of the second auxiliary member 79 and the second half portion 74. A knob 89 is placed rotatably at the outside surface of the second auxiliary member 79. As shown in FIG. 15, the rotation axis of the knob 89 projects into the interior space of the second half portion 74 and an arm portion 90 is fixed therein. As shown in FIG. 13, a locking piece 91 which projects from and enter into the second half portion 74 via a notch 74*a* formed in the second half portion 74 is fixed at the middle portion of the arm portion 90. As shown in FIG. 15, a tip side edge portion of the arm portion 90 comes into contact with a projecting portion 105 of a gate plate 102 as described below, so that this gate portion 102 can open and close. Further, a recess 90*a* is formed at the tip of the arm portion 90. This recess 90*a* engages with and detaches from the projecting portion 105 of the gate plate 102 and positions the gate plate 102 at the opening position in a state of engaging. A rectangular-like opening (not shown) is formed at the center of the division wall of the chute body 71 composed of the first half portion 73 and the second half portion 74 and a solenoid 100 is provided at a space of the back side of it as shown in FIG. 16.

As shown in FIG. 13, the slide plate 93 comprises a first guide wall 94 of the back side and a second guide wall 95 of the second half portion 74 side.

As shown in FIG. 16, a cylindrical spring receiver 96 extending upward along back surface of the body side first guide wall 94, a locking receiver 97 projecting in a roughly U-shaped form in the direction of the back surface and a detected portion 98 cylindrically projecting in the direction of the back surface are formed respectively in the body side first guide wall 94. The spring receiver 96, the locking receiver 97 and the detected portion 98 project into the space of the back side via a opening formed in the chute body 71. A coil spring 99 provided between the spring receiver 96 and the upper surface comprising the back side space of the chute body 71 is placed at the spring receiver 96. The slide plate 93 which receives the biasing force from this coil spring 98 comes contact with the convex portion 76 formed in the first half portion 73 of the chute body 71 by the side edge portion of the first guide wall 94 and is positioned at the lower position where the outer surface of the second guide wall 95 comes contact with the interior surface of the second half portion 74. A rod 101 of a solenoid 100 is engaged with and detached from the locking receiver 97. When the slide plate 93 is positioned at the upper position, the detected portion 98 is detected by the detection sensor 87.

As shown in FIG. 13, the body side second guide wall 95 is formed as a figure along the inside surface of the side wall of the cover 72 and the second half portion 74. That is, the second guide wall 95 is composed of a first straight portion 95*a*, a curved portion 95*b* continued from the lower side of the first straight portion 95*a* and a second straight portion 95*c* further continued from the lower side of the curved portion 95*b*. The slide plate 93 goes up and down along the back surface of the chute body 71. In the case that the slide plate 93 is positioned at the lower position, a tablet passage is composed of the inside surface of the second guide wall 95, the inside surface of the side wall of the first half portion 73 and the front cover 72. For details, a wide passage is formed by the first straight portion 75*a*, 95*a* and a first straight portion 112*a* as described below. In the case that the slide plate 93 is positioned at the upper position, the second straight portion 95*c* goes from the opposed position of the first straight portion 75*a*, 112*a* to the opposed position of the curved portion 75*b*, 112*b* or the second straight portion 75*c*, 112*c*. In this state, the part which cross-sectional area of the passage becomes small is lost, so that it is possible to prevent tablets from being clogged. Further, a gate plate 102 is rotatably placed at the lower portion of the first guide wall 94.

As shown in FIG. 18, the gate plate 102 has a half cylindrical shape, and the tip part of it gradually declines downward according to heading towards the tip. A rotation axis is formed at the upper portion of the gate plate 102. The rotation axis is connected to the lower portion of the first guide wall 94 of the slide plate 93. One end portion of the auxiliary plate 104 is rotatably connected to the center portion of the back side of the gate plate 102 via a pivot 104*a*. The other end portion of the auxiliary plate 104 is rotatably supported between the first half portion 73 and the second half portion 74 via a pivot 104*b*. This makes the slide plate 93 go up and down by pivot motion of the gate plate 102.

As shown in FIG. 15, one end side of the rotation axis 103 of the gate plate 102 is composed of a projecting portion 105 projecting laterally. The projecting portion 105 is pushed by the tip portion of the arm portion 90 fixed on the knob 89. The projecting portion 105 is engaged with the recess portion 90*a* of the tip of the arm portion 90, so that the gate plate 102 is positioned at the open position. As shown in FIG. 18, a locking receiver 106 projects laterally from the edge of the back side of the gate plate 102. The locking receiver 106 is formed in a roughly U-shape, so that its rigidity is increased. A curved surface is formed on the upper surface of the locking receiver 106, so that a locking projecting portion 67 provided at the chute body 71 is easily locked to the upper surface.

When the slide plate 93 is positioned at the lower position, the rotation axis of the gate plate 102 is limited to the lower side. This makes the gate plate 102 position to the close position where the lower portion of a tablet passage formed by the first half portion 73, the slide plate 93 and the cover 72 is closed. When the knob 89 is operated, the projecting portion 105 is pushed by the tip of the arm portion 90, so that the gate plate 102 is rotated from the close position to the open position. A push-receiver 108 projecting to the lower side than the lower portion is formed at the back surface of the tip side of the gate plate 102. This push receive portion 108 is pushed into by the upper opening of the tablet container 6 as well as the above embodiment, so that the gate plate 102 is rotated from the close position to the open position.

As shown in FIG. 17, the cover 72 is formed in a groove shape, and made of a material having translucency. A shoulder 109 is formed at the upper end portion of the cover 72. The shoulder 109 engages with a receive portion in the side of the tablet cassette 2. A first engaging projecting portion 110 and a second engaging projecting portion 111 are formed at the both side of the lower portion of the cover 72. Each of engaging projecting portions 110, 111 is engaged with and detached from each of engaging holes 81, 88 formed on the chute body 71 respectively. When the first engaging projecting portion 110 is inserted to the first engaging hole 81, the click portion 85 of the rotatable piece 83 is pushed and the rotatable piece 83 is rotated against the biasing force of the coil spring 84. This enables the click portion 85 of the rotatable piece 83 to release the locking state to the locking receiver 106. Therefore, it is easily possible to judge whether or not the stored tablet number is adequate and to select the tablet container 6 to dispense stored tablets.

A cover side first guide wall 112 and a cover side second guide wall 113 which forms the space reducing its section area gradually according to heading toward the lower side are formed at the inside of the side wall of the cover 72 by the body side first guide wall and the body side second guide wall 77 of the chute body 71. The cover side first guide wall 112 and the cover side second guide wall 113 are composed of first straight portions 112*a*, 113*a*, curved portions 112*b*, 113*b* and second straight portions 112*c*, 113*c* in series from the upper side. A locking receiving wall 114 is formed between the side wall and the cover side second guide wall 113. A locking piece 91 provided to the arm portion 90 which is rotated by the knob 89 can be locked to the locking receiving wall 114. As described above, the shoulder 109 and the first engaging projecting portion 110 prevent the cover 72 from departing forward against the chute body 71. The locking state prevents the cover 72 from departing downward against the chute body 71. This makes it impossible to depart the cover 72 from the chute body 71 without operating the knob 89.

With the above configuration of the cute 70, tablets of a predetermined number are dispensed from the tablet cassette 2 to the chute 70 based on the prescription data as well as the above described. In the chute 70, the gate plate 102 is positioned at the closed position and tablets dispensed from the tablet cassette 2 are stored in it. A user pushes the push-receiving portion 108 of the gate plate 102 into by the upper opening portion of the tablet container 6, so that the gate plate 102 is rotated from the closed position to the open position and the stored tablets are dispensed into the tablet container 6.

By the way, in the chute 70, when using it, fine powder from tablets may be attached to the interior surface. If utilizing the chute 70 for another kind of tablets, the problem of contamination may be occurred. As a result of this, it is needed to clean the chute 70. Thus, the cover 72 is removed from the chute body 71 and the attached fine powder is cleaned up. At this time, the knob 89 is operated and the locking piece 91 of the arm portion 90 is detached from the locking receiving wall 114 of the cover 72. This enables the cover 72 to detach from the chute body 71 by making the cover 72 slide downward against the chute body 71. The projecting portion 105 engages with the recess formed at the tip of the arm portion 90 and positioned at the open position.

When the cover 72 is detached from the chute body 71, each of the engaging projecting portions 110, 111 is detached from each of the engaging holes 81, 88 respectively at a time. When the first engaging projecting portion 110 is detached from the first engaging hole 81, the rotating piece 83 loses the support of the first engaging projecting portion 110 and rotates according to the biasing force of the coil spring 84 and after the locking projecting portion 86 locks the locking receiving portion 106 of the gate plate 102. This prevents the rotation of the gate plate 102 in addition to engagement of the recess 90*a* and the projecting portion 105, and functions as the second locking mechanism (so-called double lock mechanism). It is judged that the slide plate 93 is positioned at the upper position when the detected portion 98 is detected by the detection sensor 87. In this state, dispensing of tablets from the tablet cassette 2 is canceled based on the detection signal of the detection sensor 87.

When the cover is detached from the chute body 71, the place where the fine powder is attached by wiping and vacuuming, etc. is cleaned up. Since it can be cleaned in the state that the cover 72 which occupies all of the front side of the chute 70 is detached, it is possible to clean all area with good working efficiency.

When cleaning work is finished, the cover 72 is placed to the chute body 71. That is, the cover 72 is approached obliquely upward against the chute body 71, the shoulder 109 of the cover 72 is engaged with the receiving portion of the side of the tablet cassette 2 and each of the engaging projecting portions 110, 111 is inserted into each of the engaging holes 81, 88. When the first engaging projecting portion 110 is inserted into the first engaging hole 81, the rotating piece 83 is pushed into against the biasing force of the coil spring 99. Then, the locking projecting portion 86 is detached from the locking receiving portion 106 of the gate plate 102 and the slide plate 93 is rotated to the lower position by the biasing force of the coil spring 99. As a result, it is possible to dispense tablets from the tablet cassette 2 to the chute 70.

In addition, even if coming into contact with the knob 89 by mistake during cleaning, the gate plate 102 is maintained to the opening position and is not rotated to the close position since the locking projecting portion 86 of the rotating piece 83 is locked to the locking receiving portion 106. Thus, the detected portion 98 is not detected by the detection sensor 87, and dispensing tablets from the tablet cassette 2 is rejected.

In another possible configuration, two or more device bodies 1 are provided. In this case, the liquid crystal monitor 8 can be shared by two or more device bodies 1, and through touch operation of a screen switch button in the main screen as shown in FIG. 8, the screen may be switched to one showing the conditions of the tablet cassettes 2 of either of the device bodies 1.

In another possible configuration, the prescription number in the case that tablets are dispensed from the tablet feeder and the result calculated on a monthly basis is displayed on the screen. Moreover, the detail of dispensing can be displayed on a daily basis, weekly basis and monthly basis, etc.

Although, in the above embodiment, a solenoid unshown makes chute 3, 50, 70 be in the locking state and tablets are not dispensed without asking, a solenoid of each chute 3, 50, 70 can be freely controlled by the control unit 5. For example, it is possible to design such that the locking state of each chute 3, 50, 70 is cancelled individually or in line basis. It can be discriminated that the locking state is cancelled by changing the displaying configuration of the cassette column 41*a* displayed on the main screen 41. This enables the chute 3, 50, 70 which is desired to cancel the locking to be set arbitrarily, for example, in the case that each chute 3, 50, 70 is cleaned up, etc. and it becomes possible to respond softly according to use's needs.

Although, in the above embodiment, dispensing tablets based on prescription data is performed in the input order without the case of setting the priority order, it may be possible to set the promised prescription time and to dispense tablets of the description having a long waiting time on a priority basis (promised prescription). That is, the promised prescription time (for example, 60 minutes) is set and if the promised prescription time goes through from the time receiving the prescription data, it is preferable to perform dispensing tablets based on the prescription in priority to another prescription. This enables to prevent the problem such as being waited for a long time with respect to a certain prescription.

Although, in the above embodiment, when the demand of dispensing tablets are continued to the same tablet cassette 2 (waiting description), the number of the indicator displayed on the cassette column 41*a* of the main screen of the liquid crystal monitor 8 is only changed, the following configuration can be added.

That is, when the demand of dispensing tablets are continued to the same tablet cassette 2, if a barcode printed on a prescription is read by a barcode reader, it may be displayed on the liquid crystal panel 8 which prescription includes tablets dispensed to the chutes 3, 50, 70 at the moment. For example, if the name of the tablets dispensed to the chutes 3, 50, 70 are not coincided with the name of the tablets printed on the description, "the tablets are not dispensed" may be displayed on the liquid crystal panel 8. Moreover, the order of the prescription also may be displayed on it. That enables a user to confirm that the dispensed tablets correspond to which prescription. In addition, the case that the demand of dispensing tablets is continued corresponds to the case that normal prescription, promised prescription or property prescription is performed by itself or complex of them is continued.

Figure 25:
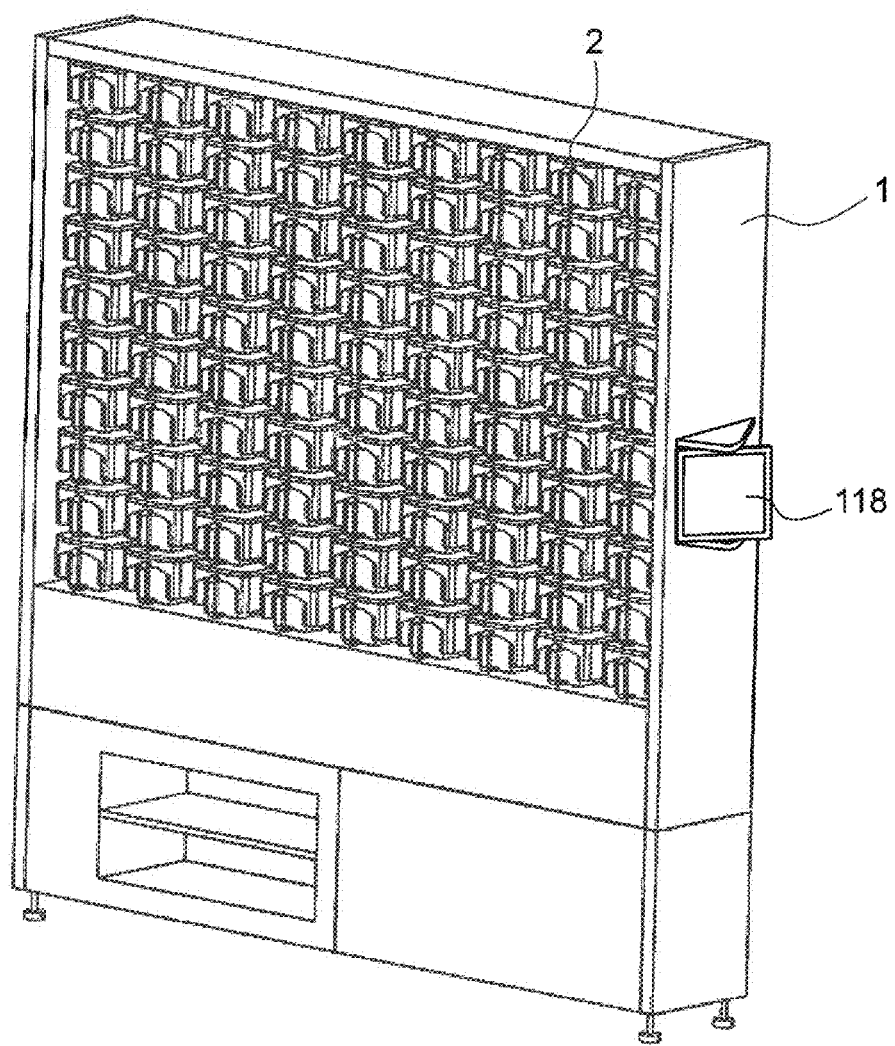
FIG. 25 is a perspective view of the tablet feeder according to another embodiment viewing from the front side thereof.
Figure 26:
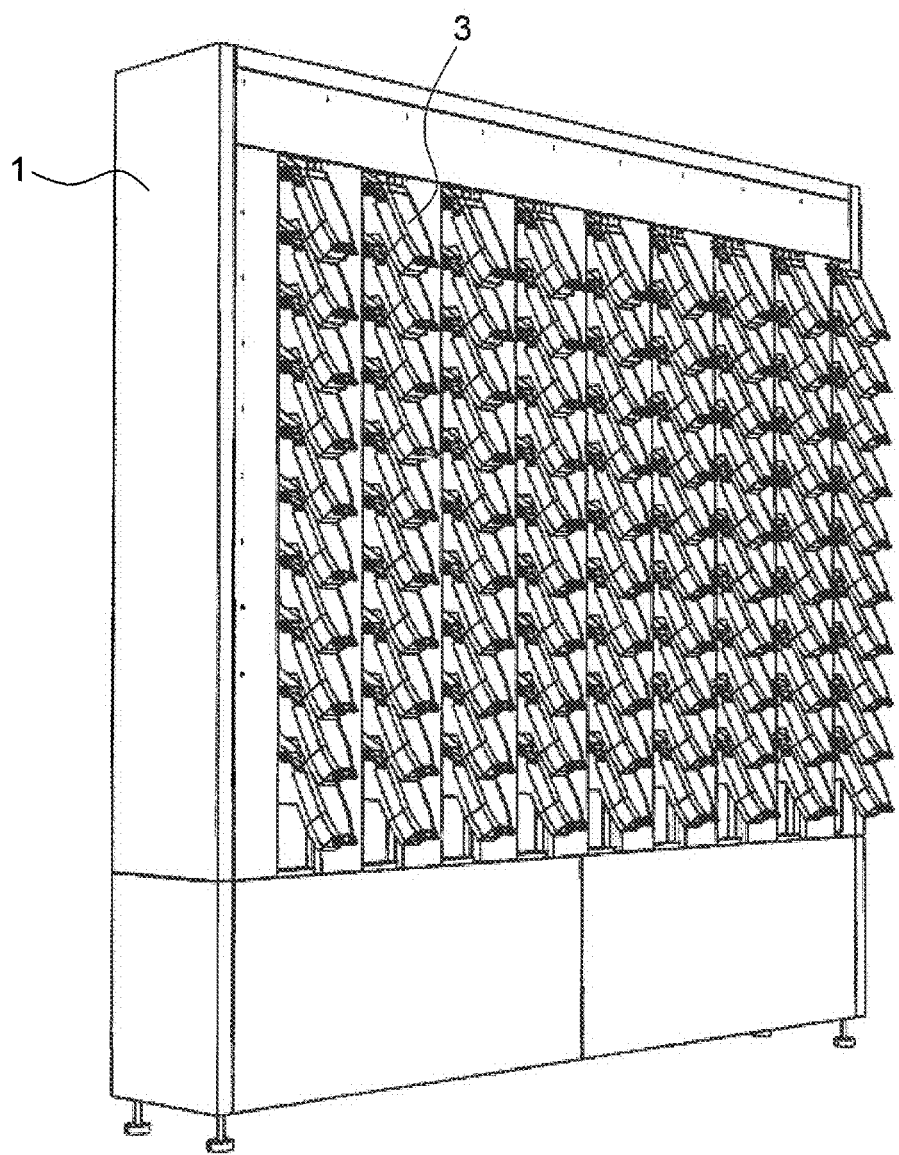
FIG. 26 is a perspective view of the tablet feeder of FIG. 25 shown from the back side.
Figure 27:
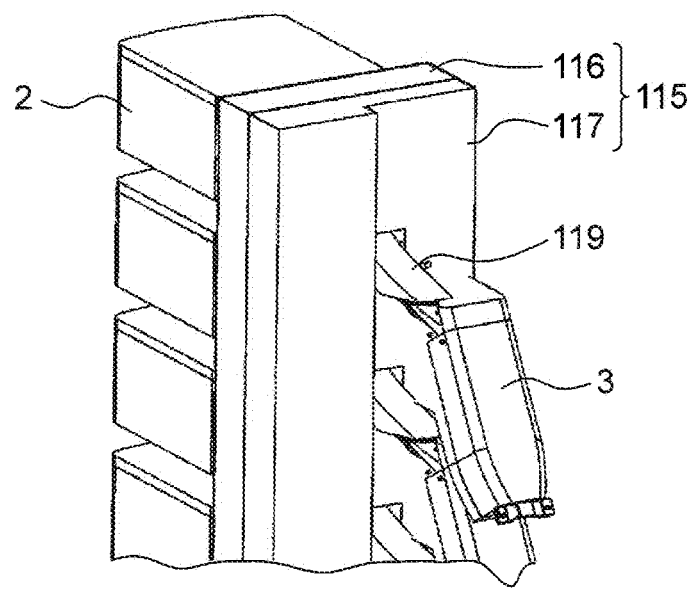
FIG. 27 is a partial perspective view of the connection structure of the chute and tablet cassette of FIG. 26.

FIGS. 25 and 26 show a tablet feeder according to another embodiment. The tablet feeder is different from that of the above each embodiment at the point of the position of the tablet cassette 2 and chute 3 provided therein. As shown in FIG. 27, the device body 1 is separated to the front side and back side by a plurality of support members 115 arranged in a horizontal direction continuously. The support member 115 is composed of a first support portion 116 configuring the front side and a second support portion 117 configuring the back side. The first support portion 116 supports the tablet cassettes 2 in a predetermined distance vertically. The support portion 117 has a passage member 119 described below protruding therefrom. Half of the support portion 117 is also formed in a stepped shape in a horizontal direction and the chutes 3 are arranged in a vertical direction therein. The device body 1 has a monitor 118 (see FIG. 25) attached to the side thereof.

As shown in FIG. 25, the tablet cassettes 2 are arranged with vertically no gaps therebetween and fixed to the first support portion 116 at each line. Only a slight gap is formed between the bottom face of the cassette body 9 of the upper side tablet cassette 2 and the upper face of the open-close lid 10 of the lower side tablet cassette 2. A predetermined gap is formed between adjacent cassettes 2 in a horizontal direction. This is due to the arrangement of the tablet cassette 2 and the chute 3 provided at the back side thereof which are shifted along a horizontal direction.

As shown in FIG. 26, the chute 3 is fixed so as to protrude in an obliquely downward direction from the second support portion 117. The upward chute 3 and the downward chute 3 are provided to overlap each other. The chute 3 is provided at the back face of the device body 1. Therefore, the filling work of tables to the tablet cassette 2 and the dispensing work of the tablets from the chute 3 are performed at the both side of the device body 1. Each chute 3 is shifted in a horizontal direction with respect to the corresponding cassette 2. (See the dashed line showing the center of each of members 2 and 3 in FIG. 28) The chute 3 is positioned lower than the corresponding cassette 2, so that tablets dispensed from the cassette 2 can move to the chute 3 under its own weight.

Figure 28:
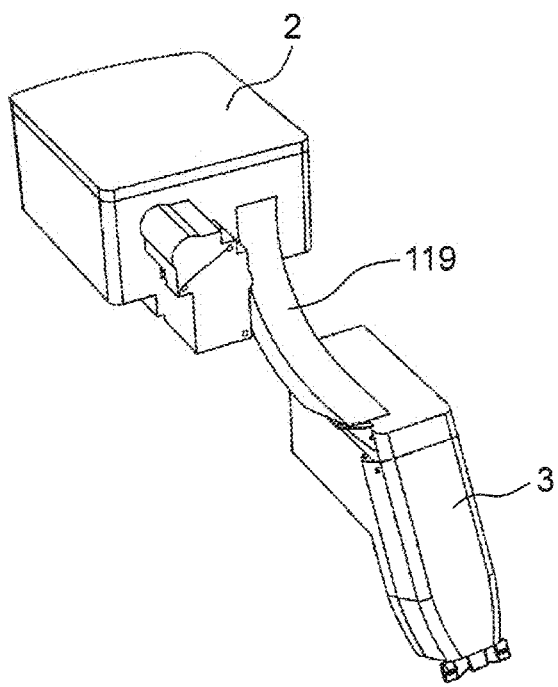
FIG. 28 is a perspective view of a pair of the tablet cassette and chute with the support member removed from FIG. 27.
Figure 29:
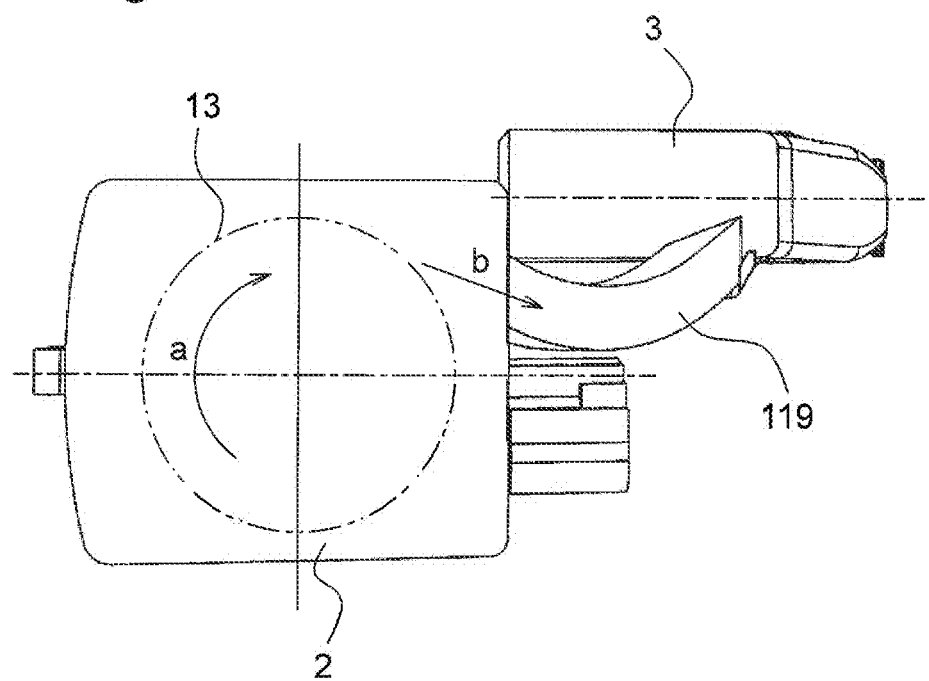
FIG. 29 is a plan view of FIG. 28.

As shown in FIG. 28, the cassette 2 and chute 3 are connected to each other through a passage member 119. One end opening of the passage member 119 is connected to the back face of the tablet cassette 2, which the other end opening is connected to the side portion of the upper face of the chute 3 through the passage of the second support portion. As shown in FIG. 28, the tablet in the cassettes 2 moves in a circumferential direction shown as an arc-like arrow "a" based on the rotation of the rotor 13 and directs to the external diameter side shown as a liner arrow "b" based on centrifugal force. Thus, the one end opening of the passage member 119 is connected to a part of the cassette 2 in the direction to which the tablet directs. Therefore, the tablet enters into the passage member 119 without reducing its moving speed. The passage member 119 is formed so as to curve its shape from the one end opening to the other end opening and also from upward to downward. This curved shape is configured in FIG. 28 to extend from the back face of the cassette 2 to the down side and direct to the upper side gradually, so that the tablet dispensed from the cassette 2 has less resistance from impact and the like when passing through the passage member. Therefore, the tablet dispensed from the cassette 2 reaches the chute 3 smoothly in a short time.

As shown in FIG. 25, the monitor 118 is pivotably attached to the side face of the device body 1. For detail, the monitor 118 is supported around a shaft which is provided on a pair of support walls and extends in a vertical direction. This allows the monitor 118 to rotate in the inclined condition toward the front and back side of the device body 1. One monitor 118 is visible from the both of the front and back side of the device body 1. The monitor 118 can be provided on the upper face of the device body 1 instead of the side face thereof, so that it becomes visible from the both of the front and back side of the device body 1.

Figure 30:
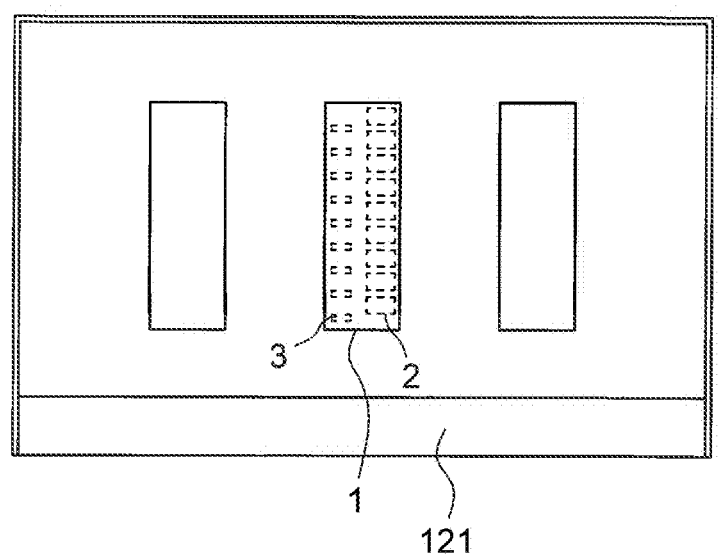
FIG. 30 is a plan view showing an example of the layout which tablet feeders according to another embodiment are located at a pharmacy.

The tablet feeder of the above configuration is disposed in a pharmacy as shown in FIG. 30. The tablet feeder is disposed across (here orthogonal to) a tablet delivery area 121 extending from one end side to the other end side in a rectangular shape. The delivery area 121 means the area for delivering a tablet container 6 in which tablets dispensed from the tablet feeder are accommodated to a patient.

The layout of the tablet feeder as described above allows an operator (a pharmacist) to fill up tablets only at the one side of the device body 1 to which tablet cassettes 2 are attached. The layout also allows the operator to dispense tablets from the tablet container 6 at the other side of the device body 1 to which the chutes 3 are attached. That is, the work of filling up and dispensing tablets can be performed at the both side of the device body 1 respectively. This allows a plurality of operators to work together and to improve operability.

Figure 31:
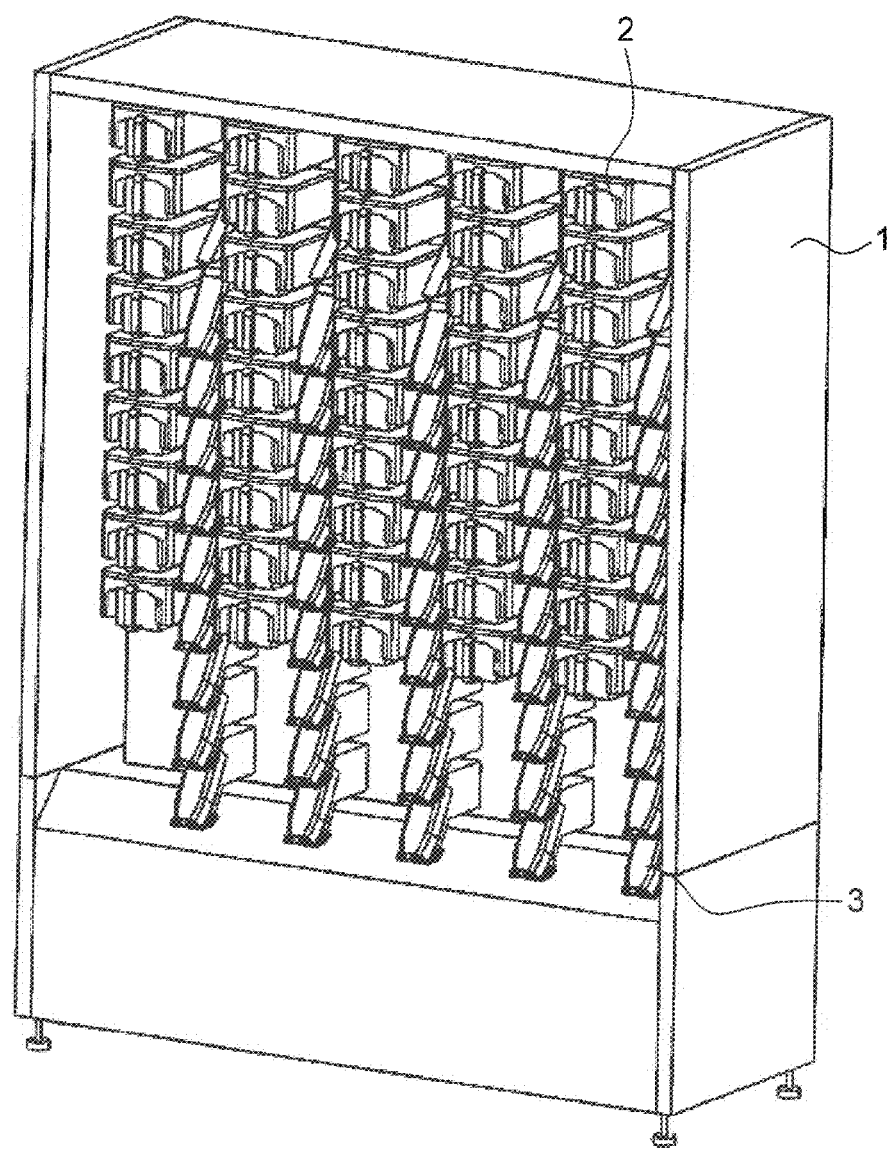
FIG. 31 is a perspective view of the tablet feeder according to another embodiment shown from the front or back side.
Figure 32:
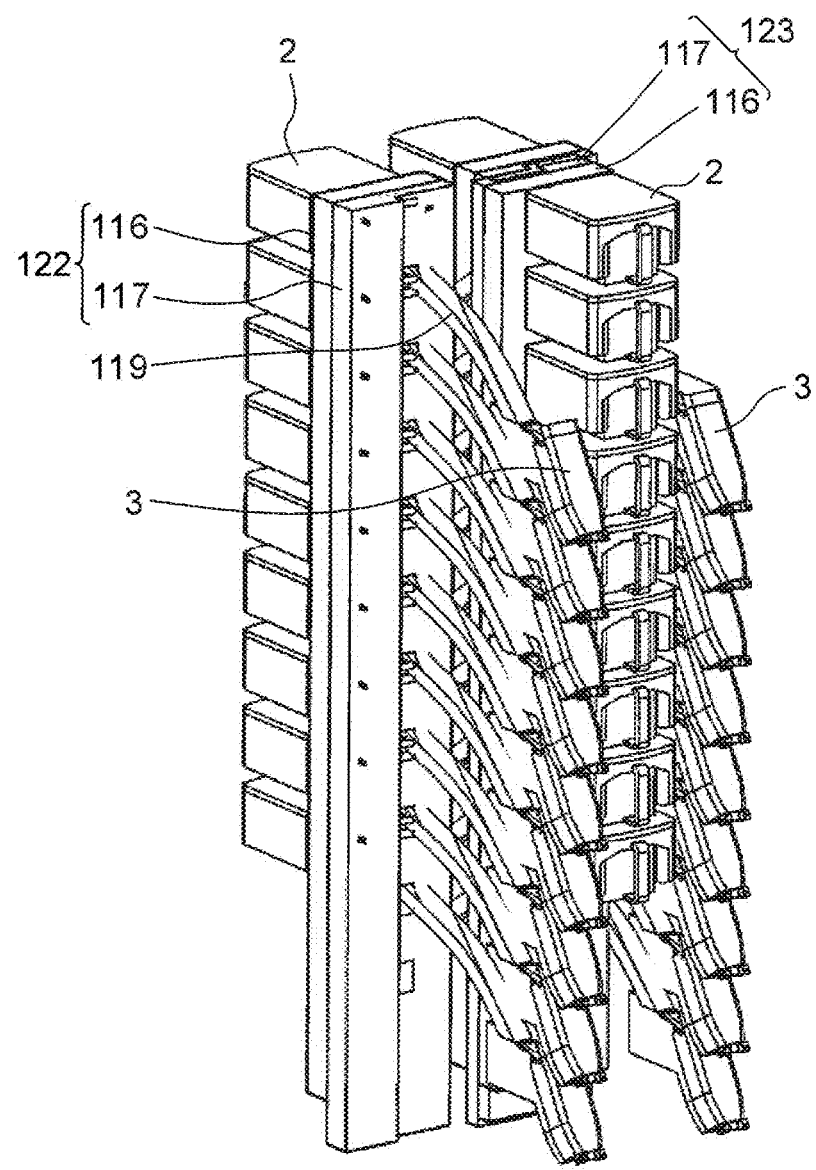
FIG. 32 shows a partial perspective view showing the connection structure of the chute and the tablets cassette of FIG. 30.

FIG. 31 further shows a tablet feeder according to another embodiment. This tablet feeder has cassettes 2 and chutes 3 at the both side of the front and back face of the device body 1 provided thereon respectively. As shown in FIG. 32, the support member 115 is configured as a first support member 122 provided on the front side of the device body 1 and a second support member 123 provided on the back side thereof. The first support member 122 and second support member 123 are configured as the first support portion 116 and the second support portion 117 similar to the above. The first support member 122 has tablet cassettes 2 provided on the front side thereof and chutes 3, which are connected to the corresponding tablet cassettes 2 respectively and supported by the tablet cassette 2 adjacent to another tablet cassette 2, provided at the back side. The second support member 123 has tablet cassettes 2 provided at the front side and chutes 3, which are connected to the tablet cassettes 2 respectively and supported by the first support member 122 adjacent to another support member 122, provided at the front side. Thus, the tablet cassettes 2 of the front and back side respectively are provided back to back. A gap is formed between the support members 115 provided in a horizontal direction. In this gap, the tablet cassettes 2 of the front side and the chutes 3 of the back side or the passage member 119 connecting the tablet cassettes 2 of the back side and the chutes 3 of the front side are provided. This allows the device body 1 to provide the chute 3, which is positioned at the right side as viewing from the front side, corresponding to the tablet cassette 2 which is positioned at the opposite side.

With the tablet feeder of the above configuration, it is possible to locate the tablet cassettes 2 and chutes 3 effectively utilizing the both space of the front and back side of the device body 1. That is, in FIG. 31, the cassettes 2 can be located at the both side of the device body 1 in the high density. Accordingly, when the medicine feeding device is located at a pharmacy, desired kind and number of tablets can be arranged in a small space without increasing number of the devices. Since the work of filling up and dispensing tablets can be performed at the both side of the device body 1, many operators can perform the work of filling up and dispensing tablets simultaneously, so that it is possible to improve operability similarly.

Although the example which only one tablet feeder shown in FIG. 25 is located at a pharmacy is explained in FIG. 30, the tablet feeder can be located more than two in the pharmacy. In this case, the cassettes 2 and chutes 3 may be positioned at the same side or at opposed side thereof.

Figure 33:
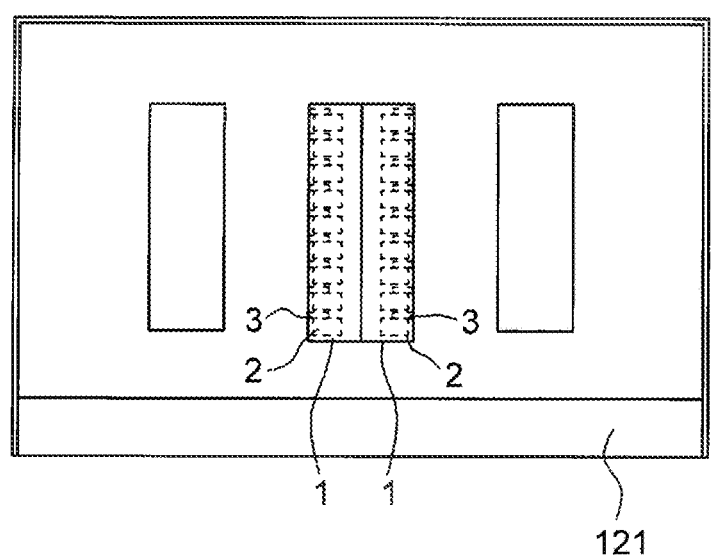
FIG. 33 shows a plan view of an example of a layout which two tablet feeders according to another embodiment are located at a pharmacy.

If the two tablet feeders are the same type which the cassettes 2 and chutes 3 are located at the same side as shown in FIG. 1, the tablets feeders may be located back to back as shown in FIG. 33. Thus, it is possible to effectively utilize the limited space in the pharmacy.

Figure 34:
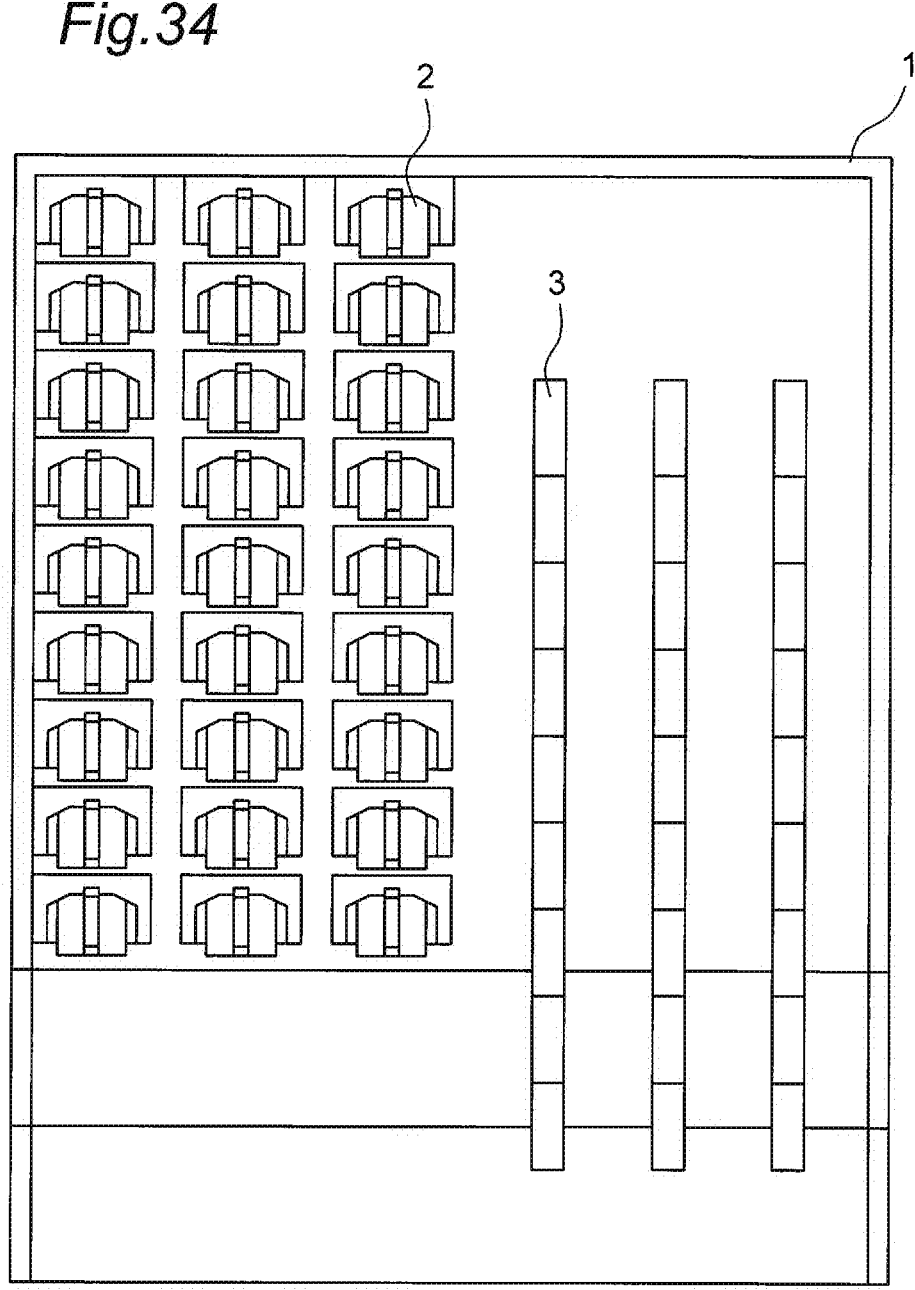
FIG. 34 shows a front view of the tablet feeder according to another embodiment.

Although the cassettes 2 and chutes 3 are located adjoiningly at the front and back side of the device body 1 in FIG. 31, the cassettes 2 and chutes 3 may be collectively located at each area which is separated in a horizontal direction at each face of the tablet feeder. That is, as shown in FIG. 34, the area at which the cassettes 2 are arranged and the area at which the chutes 3 are arranged may be located at each area separating one face of the device body 1 in a horizontal direction. In this case, it is needed to elongate the passage member connecting the tablet cassette 2 and chute 3, so that it is preferably to enlarge height difference therebetween. It is, however, possible to help the movement of tablets by supplying air into the passage.

Separating the area on which the cassettes 2 and chutes 3 are provided can make the work of filling up tablets into the tablet cassette 2 and dispensing them therefrom perform at the each separated area and proceed the work effectively.

Figure 35:
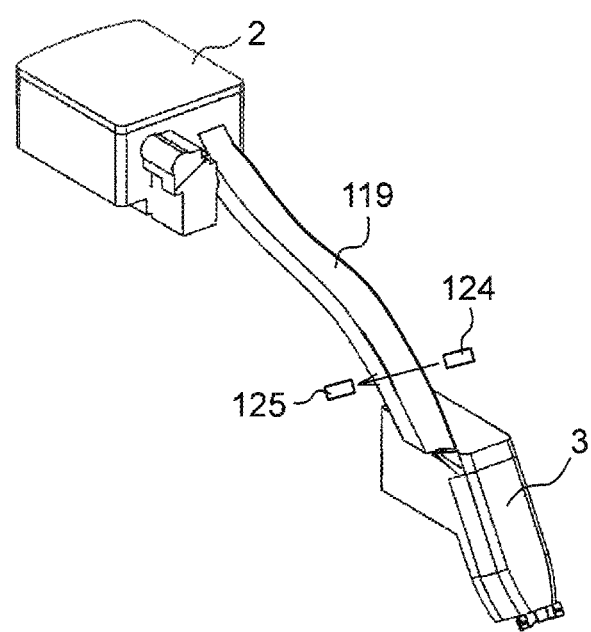
FIG. 35 shows a perspective view of the connection structure of the tablet cassettes and chutes according to another embodiment.

Although the cross section of the passage member is same as that of the passage in which the tablets move, as shown in FIG. 35, the passage member may be formed so that the cross section thereof increases gradually from the tablet cassette 2 to the chute 3. With this construction, it is possible to certainly prevent passage member from being clogged by the tablets.

It is also preferably to comprise a detection sensor for detecting the clog of the tablets in the passage. It is possible to use for example a light-emitting element 124 and a light receiving element 125 as shown in FIG. 35 similarly as a clogging detection sensor. In this case, when whole or part of the passage member 119 is configured as a material having light transmissivity, if the light from the light-emitting element 124 is interrupted and the light-receiving element 125 cannot receive the light, it can be judged that the passage is clogged by the tables.

What is claimed is:

1. A tablet feeder comprising:
    a device body having a first face and a second, opposite face;
    a first plurality of tablet cassettes disposed in a vertical direction on the first face of the device body;
    a second plurality of tablet cassettes disposed in a vertical direction on the second face of the device body, each tablet cassette of the first and second plurality of tablet cassettes accommodating a plurality of tablets;
    a first plurality of first chutes disposed in a vertical direction on the second face of the device body in a one-to-one relationship with the first plurality of tablet cassettes;
    a second plurality of first chutes disposed in a vertical direction on the first face of the device body in a one-to-one relationship with the second plurality of tablet cassettes, wherein each first chute of the first plurality of first chutes is in communication with a respective one of the first plurality of tablet cassettes and each first chute of the second plurality of first chutes is in communication with a respective one of the second plurality of tablet cassettes, each first chute of the first and second plurality of first chutes configured to temporarily store tablets disposed from a respective tablet cassette of the first and second plurality of tablet cassettes and having a dispensing portion, wherein each tablet cassette of the first and second plurality of tablet cassettes is detachably attached to the device body independent from the attachment of a corresponding first chute of the first and second plurality of first chutes to the device body; and
    a passage member for guiding the tablets dispensed from a respective tablet cassette to a second face of the device body opposite the first face, the plurality of first chutes vertically disposed on the second face capable of storing tablets dispensed from the respective tablet cassette through the passage member.

2. The tablet feeder according to claim 1, wherein the first plurality of tablet cassettes disposed on the first face are separated in a horizontal direction from the second plurality of tablet cassettes disposed on the second face; and wherein the first plurality of first chutes disposed on the first face are separated in a horizontal direction from the second plurality of first chutes disposed on the second face.

3. The tablet feeder according to claim 1, wherein a passage section of the passage member in which tablets move is formed so that its cross-sectional area widens from a respective tablet cassette toward a respective first chute.

4. The tablet feeder according to claim 1, wherein the passage member has a detection sensor for detecting a clog of tablets in the passage member.

5. The tablet feeder according to claim 1, wherein a slight gap is formed between a bottom face of an upper side tablet cassette of the first and second plurality of tablet cassettes and an upper face of a lower side tablet cassette of the first and second plurality of tablet cassettes.

6. A pharmacy system comprising:
    a tablet feeder including:
        a device body;
        a first plurality of tablet cassettes provided on a first face of the device body in a vertical direction;
        a second plurality of tablet cassettes provided on a second face of the device body in a vertical direction;
        a first plurality of chutes disposed on the second face of the device body in a vertical direction, each chute of the first plurality of chutes in communication with a respective tablet cassette of the first plurality of tablet cassettes and disposed on the second face shifted in a horizontal direction from the respective tablet cassette of the first plurality of tablet cassettes;
        a second plurality of chutes disposed on the first face of the device body in a vertical direction, each chute of the second plurality of chutes in communication with a respective tablet cassette of the second plurality of tablet cassettes and disposed on the first face shifted in a horizontal direction from the respective table cassette of the second plurality of tablet cassettes,
        wherein each chute of the first and second plurality of chutes includes a dispensing portion at a lower portion thereof capable of dispensing tablets to a cylindrically bottomed tablet container,
        wherein each tablet cassette of the first and second plurality of tablet cassettes is detachably attached to the device body independent from the attachment of a corresponding chute of the first and second plurality of chutes to the device body; and a tablet delivery area extending from a first end side to a second end side in a first direction, wherein the tablet feeder is disposed so that a first face or a face thereof is positioned perpendicular to the first direction of the tablet delivery area.

* * * * *